United States Patent
Fernandes et al.

(10) Patent No.: US 9,937,194 B1
(45) Date of Patent: Apr. 10, 2018

(54) COMPOUNDS AND METHODS FOR TREATING INFLAMMATORY DISEASES

(75) Inventors: Prabhavathi Fernandes, Chapel Hill, NC (US); David E. Pereira, Apex, NC (US)

(73) Assignee: Cempra Pharmaceuticals, Inc., Chapel Hill, NC (US)

( * ) Notice: Subject to any disclaimer, the term of this patent is extended or adjusted under 35 U.S.C. 154(b) by 0 days.

(21) Appl. No.: 13/596,875

(22) Filed: Aug. 28, 2012

Related U.S. Application Data

(63) Continuation of application No. 12/814,217, filed on Jun. 11, 2010, now abandoned.

(60) Provisional application No. 61/186,556, filed on Jun. 12, 2009.

(51) Int. Cl.
*A61K 31/7048* (2006.01)
*A61K 31/7036* (2006.01)
*A61K 31/546* (2006.01)

(52) U.S. Cl.
CPC ........ *A61K 31/7048* (2013.01); *A61K 31/546* (2013.01); *A61K 31/7036* (2013.01)

(58) Field of Classification Search
CPC .. C07H 17/08; C07H 19/056; A61K 31/7048; A61K 31/7052
USPC .................................................. 536/7.2, 7.4
See application file for complete search history.

(56) References Cited

U.S. PATENT DOCUMENTS

| | | | |
|---|---|---|---|
| 1,354,753 A | 10/1920 | Howard | |
| 2,180,006 A | 11/1939 | Hasche | |
| 3,668,282 A | 6/1972 | Below | |
| 3,843,787 A | 10/1974 | Fabrizio | |
| 4,312,866 A | 1/1982 | Caruso | |
| 4,331,803 A | 5/1982 | Watanabe | |
| 4,474,768 A | 10/1984 | Bright | |
| 4,742,049 A | 5/1988 | Baker | |
| 4,886,792 A * | 12/1989 | Djokic ................ | C07D 267/00 514/183 |
| 4,990,602 A | 2/1991 | Morimoto | |
| 5,211,955 A | 5/1993 | Legros | |
| 5,444,051 A | 8/1995 | Agouridas | |
| 5,527,780 A | 6/1996 | Agouridas | |
| 5,543,400 A | 8/1996 | Agouridas | |
| 5,614,614 A | 3/1997 | Agouridas | |
| 5,635,485 A | 6/1997 | Agouridas | |
| 5,656,607 A | 8/1997 | Agouridas | |
| 5,747,467 A | 5/1998 | Agouridas | |
| 5,760,233 A | 6/1998 | Agouridas | |
| 5,770,579 A | 6/1998 | Agouridas | |
| 5,834,428 A | 11/1998 | Drucker | |
| 5,985,844 A * | 11/1999 | Heck et al. .................. | 514/29 |
| 6,011,142 A | 1/2000 | Bonnet | |
| 6,020,521 A | 2/2000 | Randolph | |
| 6,028,181 A | 2/2000 | Or | |
| 6,096,714 A | 8/2000 | Agouridas | |
| 6,096,922 A | 8/2000 | Lal | |
| 6,121,432 A | 9/2000 | Bonnet | |
| 6,270,768 B1 | 8/2001 | OConnell | |
| 6,313,101 B1 | 11/2001 | Denis | |
| 6,395,300 B1 | 5/2002 | Liang | |
| 6,395,710 B1 | 5/2002 | Chu | |
| 6,407,074 B1 | 6/2002 | Bronk | |
| 6,407,257 B1 | 6/2002 | Agouridas et al. | |
| 6,420,535 B1 | 7/2002 | Phan | |
| 6,437,106 B1 | 8/2002 | Stoner | |
| 6,440,941 B1 | 8/2002 | Denis | |
| 6,455,505 B2 | 9/2002 | Agouridas | |
| 6,515,116 B2 | 2/2003 | Suh | |
| 6,555,524 B2 | 4/2003 | Kaneko | |
| 6,664,238 B1 | 12/2003 | Su | |
| 6,777,393 B2 * | 8/2004 | Bronk et al. .................... | 514/29 |
| 6,809,188 B1 | 10/2004 | Suh | |
| 6,849,608 B2 * | 2/2005 | Su et al. .................... | 514/29 |
| 6,890,907 B2 | 5/2005 | Speirs | |
| 7,163,924 B2 | 1/2007 | Burger | |
| 7,332,476 B2 | 2/2008 | Burger | |
| 7,375,234 B2 | 5/2008 | Sharpless | |
| 7,419,961 B2 * | 9/2008 | Napoletano et al. ........... | 514/29 |
| 7,601,695 B2 | 10/2009 | Liang | |
| 8,012,943 B2 | 9/2011 | Duffield | |
| 8,247,394 B2 | 8/2012 | Fernandes | |
| 8,791,080 B2 | 7/2014 | Fernandes | |
| 8,796,232 B2 | 8/2014 | Fernandes | |
| 9,051,346 B2 | 6/2015 | Pereira | |
| 9,200,026 B2 | 12/2015 | Liang | |
| 2002/0028781 A1 | 3/2002 | Agouridas | |
| 2002/0044967 A1 | 4/2002 | Yamashita | |
| 2003/0143162 A1 | 7/2003 | Speirs | |
| 2003/0176327 A1 | 9/2003 | Cassell | |
| 2004/0009930 A1 | 1/2004 | Su | |

(Continued)

FOREIGN PATENT DOCUMENTS

| | | |
|---|---|---|
| CN | 1343216 A | 4/2002 |
| CN | 1354753 | 6/2002 |

(Continued)

OTHER PUBLICATIONS

Amsden, Journal if Antimicrobial Chemotherapy (2005), vol. 55, pp. 10-21.*
Caira MR, "Crystalline polymorphism of orgainic compounds," Design of Organic Solids, Topics in Current Chemistry, Springer Berlin Heidelberg, 1998, p. 163-208.
Pathak et al., "Enzymatic Protecting Group Techniques in Organic Synthesis," Stereosel, Biocatal., 2000; pp. 775-797.
Katz, Leonard, and Gary W. Ashley. "Translation and protein synthesis: macrolides." Chemical reviews 105.2 (2005): 499-528.
PCT Search Report and Written Opinion for PCT/US2011/037330 completed Aug. 26, 2011.
PCT International Search Report and Written Opinion for PCT/US2011/029424, dated May 25, 2011.
Threlfall, Terence L. "Analysis of organic polymorphs. A review." Analyst 120.10 (1995): 2435-2460.

(Continued)

*Primary Examiner* — Layla D Berry
(74) *Attorney, Agent, or Firm* — Brannon Sowers & Cracraft PC

(57) ABSTRACT

Described herein are compounds and pharmaceutical compositions useful for treating inflammatory diseases.

29 Claims, No Drawings

(56) References Cited

U.S. PATENT DOCUMENTS

| | | |
|---|---|---|
| 2004/0014685 A1* | 1/2004 | Mercep .................. C07H 17/00 514/26 |
| 2005/0009764 A1 | 1/2005 | Burger et al. |
| 2005/0014706 A1 | 1/2005 | Falzari |
| 2005/0022242 A1 | 1/2005 | Rosetti |
| 2005/0153905 A1 | 7/2005 | Burger |
| 2005/0209172 A1 | 9/2005 | Woo |
| 2005/0222427 A1 | 10/2005 | Sharpless |
| 2006/0100164 A1 | 5/2006 | Liang |
| 2006/0264385 A1 | 11/2006 | Wang |
| 2007/0015719 A1 | 1/2007 | Jenkins |
| 2007/0167382 A1 | 7/2007 | Finkelstein |
| 2007/0197518 A1 | 8/2007 | Johnson |
| 2007/0281894 A1 | 12/2007 | Gant |
| 2008/0113926 A1 | 5/2008 | Ivezic |
| 2008/0221048 A1 | 9/2008 | Woo |
| 2008/0227730 A1 | 9/2008 | Mutak |
| 2008/0241959 A1 | 10/2008 | Culic |
| 2008/0287376 A1 | 11/2008 | Das |
| 2009/0005325 A1 | 1/2009 | Bas |
| 2009/0075916 A1 | 3/2009 | Upadhyay |
| 2009/0076253 A1 | 3/2009 | Kashimura |
| 2009/0087389 A1 | 4/2009 | Leonard |
| 2009/0131389 A1 | 5/2009 | Jensen |
| 2009/0156517 A1 | 6/2009 | Zhang |
| 2009/0209547 A1 | 8/2009 | Kim |
| 2010/0216731 A1 | 8/2010 | Pereira |
| 2011/0195920 A1 | 8/2011 | Fernandes |
| 2012/0071429 A1 | 3/2012 | Duffield |
| 2012/0172323 A1 | 7/2012 | Fernandes |
| 2012/0231995 A1 | 9/2012 | Beck |
| 2013/0011453 A1 | 1/2013 | Latta |
| 2013/0018008 A1 | 1/2013 | Pereira |
| 2013/0045937 A1 | 2/2013 | Pereira |
| 2013/0053362 A1 | 2/2013 | Castro |
| 2013/0102523 A1 | 4/2013 | Bartizal |
| 2013/0156705 A1 | 6/2013 | Zhang |
| 2013/0164351 A1 | 6/2013 | Fernandes |
| 2013/0172280 A1 | 7/2013 | Pereira |
| 2013/0345410 A1 | 12/2013 | Liang |
| 2014/0088062 A1 | 3/2014 | Pereira |
| 2014/0148431 A1 | 5/2014 | Patel |

FOREIGN PATENT DOCUMENTS

| | | |
|---|---|---|
| CN | 101045063 | 10/2007 |
| EP | 0248279 A2 | 12/1987 |
| EP | 0680967 A1 | 11/1995 |
| EP | 1024145 A2 | 8/2000 |
| EP | 1167375 | 1/2002 |
| GB | 891817 | 3/1960 |
| JP | S59175414 | 10/1984 |
| JP | 06220082 | 8/1994 |
| JP | 08053489 | 2/1996 |
| JP | 2000507573 | 6/2000 |
| JP | 2000229993 | 8/2000 |
| JP | 2000351794 | 12/2000 |
| JP | 2002514197 | 5/2002 |
| JP | 2004502736 | 1/2004 |
| JP | 2006528667 | 12/2006 |
| JP | 2007536371 | 12/2007 |
| JP | 2008519788 | 6/2008 |
| JP | 2008526948 | 7/2008 |
| JP | 2008534504 | 8/2008 |
| JP | 2009500356 | 1/2009 |
| JP | 2009502788 | 1/2009 |
| JP | 5914335 | 5/2016 |
| RU | 2230748 | 6/2004 |
| WO | 1997036912 | 10/1997 |
| WO | 9830574 A1 | 7/1998 |
| WO | 9856800 A1 | 12/1998 |
| WO | 1998056801 | 12/1998 |
| WO | 9921866 A1 | 5/1999 |
| WO | 9928311 A1 | 6/1999 |
| WO | 0012521 A1 | 3/2000 |
| WO | 200031099 A1 | 6/2000 |
| WO | 0044761 A2 | 8/2000 |
| WO | 0062783 A2 | 10/2000 |
| WO | 0110878 | 2/2001 |
| WO | 0110878 A1 | 2/2001 |
| WO | 2001010787 | 2/2001 |
| WO | 0250092 A1 | 6/2002 |
| WO | 03004509 A2 | 1/2003 |
| WO | 2003004509 | 1/2003 |
| WO | 03072141 A1 | 9/2003 |
| WO | 2004080391 A2 | 9/2004 |
| WO | 2004101587 | 11/2004 |
| WO | 2005074945 | 8/2005 |
| WO | 05105821 | 11/2005 |
| WO | 2005108412 | 11/2005 |
| WO | 2006050941 | 5/2006 |
| WO | 2006050942 | 5/2006 |
| WO | 2006087642 | 8/2006 |
| WO | 2007008537 | 1/2007 |
| WO | 2007059307 A2 | 5/2007 |
| WO | 2007060627 | 5/2007 |
| WO | WO 2007060627 A2 * | 5/2007 ......... A61K 31/7056 |
| WO | 20070143507 | 12/2007 |
| WO | 2009055557 | 4/2009 |
| WO | 2009055557 A1 | 4/2009 |
| WO | 2010048599 | 4/2010 |
| WO | 2010048600 | 4/2010 |
| WO | 2010048601 | 4/2010 |
| WO | 2011008193 | 1/2011 |
| WO | 2011032052 | 3/2011 |
| WO | 2011112864 A1 | 9/2011 |
| WO | 2011119604 | 9/2011 |
| WO | 2011146829 | 11/2011 |
| WO | 2012042534 | 4/2012 |
| WO | 2013148891 | 10/2013 |
| WO | 2014145210 | 9/2014 |
| WO | 2014152326 | 9/2014 |
| WO | 2014165792 | 10/2014 |
| WO | 20150123256 | 8/2015 |
| WO | 2015181723 | 12/2015 |
| WO | 2016022658 | 2/2016 |
| WO | 2016144833 | 9/2016 |

OTHER PUBLICATIONS

Petit, Samuel, and Gérard Coquerel. "The amorphous state." Polymorphism: In the Pharmaceutical Industry 10 (2006): 1.

Organic Compounds Crystal Manufacture Handbook—Principles and Knowhow, 2008, pp. 57 to 84.

Hancock, Bruno C., Sheri L. Shamblin, and George Zografi. "Molecular mobility of amorphous pharmaceutical solids below their glass transition temperatures." Pharmaceutical research 12.6 (1995): 799-806.

Ashizawa, Kazuhide, "Physico-Chemical Studies on the molecular Details of Drug Crystals," Phar Tech Japan, 2002, vol. 18, No. 10. pp. 81-96.

PCT Search Report and Written Opinion prepared for PCT/US2009/061978 dated Dec. 9, 2009.

European Search Report for EP 09 82 2827, dated Mar. 21, 2012.

International Search Report for PCT/US2009/061977, dated Dec. 23, 2009, (3 pages).

PCT Search Report/Written Opinion prepared for PCT/US2010/048540, dated Oct. 21, 2010.

Byrn, S., Pfeiffer, R., Ganey, M., Hoiberg, C., & Poochikian, G. (1995). Pharmaceutical solids: a strategic approach to regulatory considerations. Pharmaceutical research, 12(7), 945-954.

Sumerkan, B., Aygen, B., Doganay, M., & Sehmen, E. (1996). Antimicrobial susceptibility of Bacillus anthracis against macrolides. Salisbury Med Bull Supplement, 87, 138.

Maurin, M., Mersali, N. F., & Raoult, D. (2000). Bactericidal activities of antibiotics against intracellular Francisella tularensis. Antimicrobial agents and chemotherapy, 44(12), 3428-3431.

Luna, V. A., King, D. S., Gulledge, J., Cannons, A. C., Amuso, P. T., & Cattani, J. (2007). Susceptibility of Bacillus anthracis, Bacillus cereus, Bacillus mycoides, Bacillus pseudomycoides and Bacillus thuringiensis to 24 antimicrobials using Sensititre® automated

(56) References Cited

OTHER PUBLICATIONS microbroth dilution and Etest® agar gradient diffusion methods. Journal of antimicrobial chemotherapy, 60(3), 555-567.
Barthel, D., Schlitzer, M., & Pradel, G. (2008). Telithromycin and quinupristin-dalfopristin induce delayed death in Plasmodium falciparum. Antimicrobial agents and chemotherapy, 52(2), 774-777.
Still, J. G., et al. "Single Oral Dose Pharmacokinetics and Safety of CEM-101 in Healthy Subjects." 46th Annual Meeting. Idsa, 2008.
Lee, Joo Hyun, and Myung Gull Lee. "Dose-dependent pharmacokinetics of telithromycin after intravenous and oral administration to rats: contribution of intestinal first-pass effect to low bioavailability." J. Pharm. Pharm. Sci 10 (2007): 37-50.
Chen, M., Muri, E. M., Jacob, T. M., & Williamson, J. S. (2003). Synthesis and bioactivity of erythromycin derivatives. Medicinal chemistry research, 12(3), 111-129.
Kerdesky, F. A., Premchandran, R., Wayne, G. S., Chang, S. J., Pease, J. P., Bhagavatula, L., . . . & King, S. A. (2002). Synthesis of 2'-O-Benzoyl-3-keto-6-O-propargyl-11, 12-carbamoyl Erythromycin A. Organic process research & development, 6(6), 869-875.
Zhu, Z. J., Krasnykh, O., Pan, D., Petukhova, V., Yu, G., Liu, Y., . . . & Franzblau, S. G. (2008). Structure-activity relationships of macrolides against *Mycobacterium tuberculosis*. Tuberculosis, 88, S49-S63.
International Search Report Written Opinion for PCT/US2008/080936 completed Dec. 8, 2008.
Putnam S. D. et al, Antimicrobial Characterization of Solithromycin (Cem-101), A Novel Fluroroketolide: Activity Against Staphlococci and Enterococci. International Journal of Antimicrobial Agents, vol. 37, No. 1, 2011, pp. 39-45.
Written Opinion, Singapore Application No. 11201405895U; Intellectual Property Office of Singapore; dated Mar. 31, 2015, 6 pages.
Database WPI Week 200822 Thomson Scientific, London, GB; AN 2008-D02982.
Zimmermann, Torsten, et al. "Comparative tolerability of intravenous azithromycin, clarithromycin and erythromycin in healthy volunteers." Clinical Drug Investigation 21.8 (2001): 527-536.
Luke, D. R., and G. Foulds. "Toleration of intravenous azithromycin." The Annals of pharmacotherapy 31.9 (1997): abstract only.
Cannon, John B., N. Adeyinka Williams, and Karen J. Papp. "Reduction of pain on intravenous infusion with bile salt formulations for a macrolide antibiotic." International journal of pharmaceutics 114.1 (1995): abstract only.
Lu, Yan, YanJiao Wang, and Xing Tang. "Formulation and thermal sterile stability of a less painful intravenous clarithromycin emulsion containing vitamin E." International journal of pharmaceutics 346.1 (2008): abstract only.
Llano-Sotelo, B., D. Klepacki, and A. S. Mankin. 2008. Binding and action of CEM-10, a new macrolide/ketolide in development for treating infections with macrolide-resistant and macrolide-susceptible bacteria. 48th Annu. Intersci. Conf. Antimicrob. Agents Chemother./46th Infect. Dis. Soc. Am. Ann. Meet., abstr. F1-3983.
International Search Report for PCT/US2015/015353, dated May 14, 2015, (8 pages).
Ferris, C. F., Lu, S. F., Messenger, T., Guillon, C. D., Heindel, N., Miller, M., . . . & Simon, N. G. (2006). Orally active vasopressin V1a receptor antagonist, SRX251, selectively blocks aggressive behavior. Pharmacology Biochemistry and Behavior, 83(2), 169-174.
Amsden, G. W. "Anti-inflammatory effects of macrolides an underappreciated benefit in the treatment of community-acquired respiratory tract infections and chronic inflammatory pulmonary conditions?." Journal of Antimicrobial Chemotherapy 55.1 (2005): 10-21.
de Jong, J. T., et al. "[Large-scale, acute, bacterial gastroenteritis caused by the enterotoxin of *Staphylococcus aureus* after a barbecue]." Nederlands tijdschrift voor geneeskunde 148.43 (2004): 2136-2140.

Raj, Pushker. "Pathogenesis and laboratory diagnosis of *Escherichia coli* associated enteritis." Clinical microbiology Newsletter 15.12 (1993): 89-93.
Ikeue, T., et al. "[Pneumonia caused by Nocardia nova]." Nihon Kokyuki Gakkai zasshi= the journal of the Japanese Respiratory Society 39.7 (2001): 492-497.
Thakkar, Shyam, and Radheshyam Agrawal. "A case of *Staphylococcus aureus* enterocolitis: a rare entity." Gastroenterology & hepatology 6.2 (2010): 115-117.
Wain, Harry, and Paul A. Blackstone. "Staphylococcal gastroenteritis." The American journal of digestive diseases 1.10 (1956): 424.
Boyce, Thomas G., "Staphylococcal Food Poisoning," Merck Manuals (2015) 2 pages.
Lv Yang et al., "Polymorphic Drugs." Oct. 31, 2009, pp. 110-111.
LeMahieu, R. A., Carson, M., and Kierstead, R. W., 'Glycoside Cleavage Reactions on erythromycin A. Preparation of Erythronolide A,' Journal of Medicinal Chemistry, vol. 17, No. 9, 1974, 953-956.
Romero et al., 'An efficient entry to new sugar modified ketolide antibiotics' Tetrahedron Letters, vol. 46, 2005, pp. 1483-1487.
Birkenmeyer, R. D., Kroll, S. J., Lewis, C., Stern, K. F., and Zurenko, G. E., 'Synthesis and Antibacterial Activity of Clindamycin Analogues: Pirlimycin, a Potent Antibacterial Agent', Journal of Medicinal Chemistry, vol. 27, No. 2, 1984, 216-223.
Vince, R., Almquist, R. G., Ritter, C. L., and Daluge, S., Antimicrobial Agents and Chemotherapy, vol. 8, No. 4, 1975, 439-443.
Or et al., 'Design, Synthesis, and Antimicrobial Activity of 6-0-Substituted Ketolides Active Against Resistant Respiratory Tract Pathogens', J. Med. Chem., 43:1045-49 (2000).
Champney et al., 'Structure-Activity Relationships for Six Ketolide Antibiotics', Current Microbiology, 42:203-10 (2001).
Denis et al., beta-Keto-Ester Chemistry and Ketolides. Snythesis and antibacterial Activity of 2-Halogeno, 2-Methyl and 2,3 Enol-Ether Ketolides, Bioorganic & Medicinal Chemistry Letters, 10:2019-22 (2000).
Torne et al. 'Peptidotriazoles on Solid Phase: [1,2,3]-Triazoles by Regiospecific Copper(I)-Catalyzed 1,3-Dipolar Cycloadditions of Terminal Alkynes to Azides', J. Org. Chem., 67:3057-64 (2002).
Rostovtsev, V.V. et al., 'A Stepwise Huisgen Cycloaddition Process: Copper(I)=Catalyzed Regioselective 'Ligation' of Azides and Terminal Alkynes,' Angew. Chem. Int. Ed., 41: 2596-2599 (2002).
Baker, W.R. et al., 'Modification of macrolide antibiotics. Synthesis of 11-deoxy-11-(carboxyamino)-6-0-methylerythromycin A 11,12-(cyclic esters) via an intramolecular Michael reaction of O-carbamates with an alpha , beta-unsaturated ketone,' J. Org. Chem., 53:2340-2345, 1988.
Djokic, S. et al., 'Erythromycin Series. Part 11. Ring Expansion of Erythromycin A Oxime by the Beckmann Rearrangement.' J. Chem. Soc Perkin Trans 1., 1881-1890 (1986).
Phan, L.T. et al., 'Synthesis of 2-Fluoro-6-O-propargyl-11,12-carbamate Ketolides. A Novel Class of Antibiotics,' Org. Ltrs., 2:2951-2954 (2000).
Liang C. H. et al., 'Synthesis and biological activity of new 5-0-sugar modified ketolide and 2-fluoro-ketolide antibiotics,' Bioorganic & Medicinal Chemistry Letters, Pergamon, Elsevier Science, GB, vol. 15, No. 5, Mar. 1, 2005, pp. 1307-1310.
Plata et al., "The synthesis of ketolide antibiotic ABT-773 (cethromycin)," Tetrahedron, vol. 60, 2004, pp. 10171-10180.
Ma et al., Curr. Med. Chem., "Anti-Infective Agents," vol. 1, 2002, pp. 15-34.
Holzer, G., et al., "Kα1,2 and Kβ1,3 X-Ray Emission Lines of the 3d Transition Metals", Dec. 1997, Physical Review, vol. 56, No. 6, pp. 4554-4568.
Jones et al.: 'MIC Quality Control Guidelines and Disk Diffusion Test Optimization for CEM-101, a Novel Fluoroketolide' Journal of Clinical Microbiology vol. 48, No. 4, Dec. 30, 2009, pp. 1470-1473.
Berge, Stephen M., et al., "Pharmaceutical Salts", 1977, Journal of Pharmaceutical Sciences, vol. 66, No. 1, pp. 1-19.
Bermudez, Luiz E., et al., "Telithromycin is Active Against Mycobacterium Avium in Mice Despite Lacking Significant Activity in Standard in Vitro and Macrophage Assays and Is Associated

(56) References Cited

OTHER PUBLICATIONS with Low Frequency of Resistance During Treatment," 2001, Antimicrobal Agents and Chemotherapy, vol. 45, No. 8, pp. 2210-2214.
Bermudez, Luiz E., et al., "EDP-420, a Bicyclolide (Bridged Bicyclic Macrolide), Is Active Against *Mcyobacterium avium*", 2007, Antimicrobal Agents and Chemotherapy, vol. 51, No. 5, pp. 1666-1670.
Cynamon, M. H., et al., "Activity of ABT-773 Against *Mycobacterium avium* Complex in the Beige Mouse Model", 2000, Antimicrobal Agents and Chemotherapy, vol. 44, No. 10, pp. 2895-2896.
Patel, Ramesh N., "Stereoselective Biocatalysis", 2000, Bristol-Myers Squibb Research Institute; pp. 775-797.
Vennerstrom, Jonathan L., et al., "Identification of an Antimalarial Synthetic Trioxolane Drug Development Candidate", 2004, Letters to Nature, vol. 430, pp. 900-904.
Barcia-Macay, Maritza, et al., 'Pharmacodynamic Evaluation of the Intracellular Activities of Antibiotics Against *Staphylococcus aureus* in a Model of THP-1 Macrophages', 2006, Antimicrobial Agents and Chemotherapy. vol. 50, No. 3, pp. 841-851.
Bebear, C.M., et al., In vitro activity of trovafloxacin compared to those of five antimicrobials against mycoplasmas including Mycoplasma hominis and Ureaplasma urealyticum fluoroquinolone-resistant isolates that have been genetically characterized, Antimicrob Agents Chemother 44:2557-2560 (2000).
Duffy, L., et al., Fluoroquinolone resistance in Ureaplasma parvum in the United States, J Clin Microbiol 44:1590-1591 (2006).
Waites, K.B., et al., Mycoplasmas and ureaplasmas as neonatal pathogens, Clin Microbiol Rev 18:757-89 (2005).
Zuckerman, "Macrolides and ketolides: azithromycin, clarithromycin, telithromycin", Infectious Disease Clinics of North America, vol. 18, (2004), pp. 621-649.
Crone, Julia, et al., "Evaluation of a monoclonal antibody-based test for detection of Helicobacter pylori-Specific Antigen in stool samples from mice," Jul. 2004, Clinical and Diagnostic Laboratory Immunology, vol. 11, No. 4, pp. 799, 800.
Laine, Loren, et al., "Prospective comparison of H&E, Giemsa and Genta stains or the diagnosis of Helicobacter pylori," 1997, Gastrointestinal Endoscopy, vol. A 5, No. 6, pp. 463-467.
Lee, Adrian, et al., "A standard mouse model of Helicobacter pylori infection: introducing the Sydney Strain," 1997, Gastroenterology, vol. 112, pp. 1386-1397.
Drusano, G. L., et al., "Is 60 Days of Ciprofloxacin Adminstration Necessary for Postexposure Prophylaxis for Bacillus Anthracis?", 2008, Antimicrobial Agents and Chemotherapy. vol. 52, No. 11, pp. 3973-3979.
Feder, P. I., et al., 1991. Statistical Analysis of Dose-Response Experiments by Maximum Likelihood Analysis and Iteratively Reweighted Nonlinear Least Squares Regression Techniques, 1991, Drug Information Journal, vol. 28, pp. 323-334.
Inglesby, Thomas V., et al., "Anthrax as a Biological Weapon, 2002", 2002, Journal of the American Medical Association, vol. 287, No. 17, pp. 2236-2252.
Celebuski, J.E. et al., 'Chemical Modification of Erythromycin: Novel Reaction observed by Treatment with Metalloporphyrins', vol. 35, No. 23, pp. 3837-3850, 994, Elsevier Science Ltd.
Morimoto S. et al., 'Chemical Modification of Erythromycins VII. Molecular Rearrangement Observed During Chemical Modification Study of the Desosamine Unit of Erythromycins', Heterocycles, Elsevier Science Publishers, vol. 31, No. 2, Jan. 1, 1990, pp. 305-319.
Hill, D.R. et al., 'Novel Macrolides via meso-Tetraarylmetalloporphyrin Assisted Oxidation', Tetrahedron Letters, vol. 37, No. 6, pp. 787-790, 1996, Elsevier Science Ltd.
Physicians' Desk Reference, p. 2905, (2007).
Nilius et al.: 'Ketolides: the future of the macrolides?' Current Opinion in Pharmacology, [Online] vol. 2, Jan. 14, 2002, pp. 1-8 Retrieved from the Internet: <URL:http://www.sciencedirect.com/science/article/pii/S1471489202001984>.
Jensen, J.S., et al., Azithromycin Treatment Failure in Mycoplasma genitaliumPositive Patients with Nongonococcal Urethritis Is Associated with Induced Macrolide Resistance, Clin Infect Dis 47:1546-53 (2008).
Li, X., et al., Emerging macrolide resistance in Mycoplasma pneumoniae in children: detection and characterization of resistant isolates, Pediatr Infect Dis J, p. 28:693-696 (2009).
Lemaire, Sandrine, et al., "Cellular Accumulation and Pharmacodynamic Evaluation of the Intracellular Activity of CEM-101, a Novel Fluoroketolide, Against *Staphylococcus aureus*, Listeria Monocytogenes and Legionella Pneumophila in Human THP-1 Macrophages", 2009, Antimicrobial Agents and Chemotherapy. vol. 53, No. 9, pp. 3734-3743.
Le Loir, Yves, Florence Baron, and Michel Gautier. "*Staphylococcus aureus* and food poisoning." Genet Mol Res 2.1(2003): 63-76.
Brittain HG editor "Polymorphism in pharmaceutical solids", Chapter 1, p. 1-10 (Grant DJW) and Chapter 5, p. 183 "" 226 (1999).
Graeme, A. O'May, Nigel Reynolds, and George T. Macfarlane. "Effect of pH on an in vitro model of gastric microbiota in enteral nutrition patients." Applied and environmental microbiology 71.8 (2005): 4777-4783.
Cotter, Paul D., and Colin Hill. "Surviving the acid test: responses of gram-positive bacteria to low pH." Microbiology and Molecular Biology Reviews 67.3 (2003): 429-453.
Lyczak, J. B., Cannon, C. L., & Pier, G. B. (2002). Lung infections associated with cystic fibrosis. Clinical microbiology reviews, 15(2), 194-222.
Denis, Alexis, et al. "Synthesis and antibacterial activity of HMR 3647 a new ketolide highly potent against erythromycin-resistant and susceptible pathogens." Bioorganic & medicinal chemistry letters 9.21 (1999): 3075-3080.
Bryskier, A. "Ketolides"'telithromycin, an example of a new class of antibacterial agents." Clinical Microbiology and Infection 6.12 (2000): 661-669.
Morimoto, Shigeo, et al. "Chemical modification of erythromycins. I. Synthesis and antibacterial activity of 6-O-methylerythromycins A." The Journal of antibiotics 37.2 (1984): 187-189.
Hällgren, Anita, et al. "Antimicrobial susceptibility patterns of enterococci in intensive care units in Sweden evaluated by different MIC breakpoint systems." Journal of Antimicrobial Chemotherapy 48.1 (2001): 53-62.
Fernandes, P., et al. Intravenous Formulation of Solithromycin, a Painless Macrolide Antibiotic in a Rabbit Intravenous Injection Model, 2011, 5 pages.
Allen Loyd V Jr, Acidifying Agents, Featured Excipient. International Journal of Pharmaceutical Compounding, Dec. 31, 1999, vol. 3, No. 4, pp. 309 (abstract only).
Yatin R. G. et al., Excipients for Protein Drugs. Excipient Development for Pharmaceutical, Biotechnology, and Drug Delivery Systems, Jul. 28, 2006, pp. 299-300.
Fernandes, P., et al. "Solithromycin Macrolide Antibiotic." Drugs of the Future 36.10 (2011): 751-758.
Raoul, Jennifer M., Marc R. Peterson, and Theresa C. Peterson. "A novel drug interaction between the quinolone antibiotic ciprofloxacin and a chiral metabolite of pentoxifylline." Biochemical pharmacology 74.4 (2007): 639-646.
Salzer, W. (2005). Antimicrobial-resistant gram-positive bacteria in PD peritonitis and the newer antibiotics used to treat them. Peritoneal Dialysis International, 25(4), 313-319.
Caplus abstract of WO 01/10878, Accession No. 2001 :115160 (2001 ).

\* cited by examiner

COMPOUNDS AND METHODS FOR TREATING INFLAMMATORY DISEASES

CROSS-REFERENCE TO RELATED APPLICATIONS

This application is a continuation of U.S. application Ser. No. 12/814,217, filed Jun. 11, 2010, which claims priority under 35 U.S.C. § 119(e) to U.S. Patent Application Ser. No. 61/186,556 filed Jun. 12, 2009, the entirety of each of the disclosures of which are hereby incorporated herein by reference.

TECHNICAL FIELD

The invention described herein pertains to compounds, compositions, and methods for treating inflammatory diseases. In particular, the invention described herein pertains to macrolide compounds and compositions, and methods for using them for treating inflammatory diseases.

BACKGROUND AND SUMMARY OF THE INVENTION

COPD is a major and increasing global health problem, which is currently the fourth most common cause of death and is predicted to become the fifth most common cause of chronic disability in the next few years. Despite recognition as an increasingly important international health problem, current treatments for COPD are inadequate, owing in part to a fundamental lack of knowledge about the cellular, molecular and genetic causes of COPD.

The mechanisms leading to increased airway inflammation in COPD patients are complex, and in contrast to asthma, may not be inhibited by corticosteroid treatment. It has been observed that HDAC2 transcription levels, as well as HDAC2 protein expression, are reduced in severe COPD patients, particularly in the lungs, airways, and alveolar macrophages of those patients. Without being bound by theory, it is believed herein that the reduced levels may be due to proteasomal degradation. In addition, it has been discovered that oxidative stress and hypoxic condition may reduce HDAC2 promoter activation. It has also been discovered that the reduction of promoter activity or HDAC activity under oxidative stress may be normalized by phosphoinositide-3-kinase (PI3K) inhibitors and Akt inhibitors. It has also been discovered that the expression of specific inflammatory genes is increased, including CXC chemokines, such as IL-8 and GRO-α, TNF-α, and matrix metalloproteinase-9 (MMP-9). Further, it has been discovered that the reduced HDAC2 activity and expression may lead to both the observed increased expression of inflammatory genes and the decreased response to corticosteroids (see, e.g., Ito et al., N Engl J Med (2005); Ito et al., J Exp Med (2006)). The disclosure of the foregoing publication, and each publication cited herein, is incorporated herein by reference.

In laboratory tests, it has been reported that $H_2O_2$ treatment induces corticosteroid insensitivity on TNF-α-induced IL-8 production in a human macrophage cell line (U937 cells). Erythromycin has been reported to restore corticosteroid sensitivity. Erythromycin has also been reported to restore corticosteroid sensitivity seen in peripheral blood mononuclear cells (PBMCs) obtained from COPD patients. Furthermore erythromycin inhibited MMP9 expression in macrophages present in the sputum of COPD patients. Erythromycin has also been reported to restore HDAC2 promoter activity and protein expression that are reduced by oxidative stress. However, erythromycin has been reported to lack sufficient in vivo efficacy.

In addition, it is appreciated herein that the chronic treatment that would be necessary to treat patients suffering from COPD and other inflammatory diseases may not amenable to the use of erythromycin, and other compounds with substantial antibacterial or antibiotic activity, due to the potential for resistance development by bacteria and other pathogens against those compounds.

It has been discovered herein that compounds described herein are useful in treating inflammatory diseases. In one illustrative and non-limiting embodiment of the invention, compounds, compositions, and methods are described herein for treating and/or prevention of inflammatory diseases. Illustrative inflammatory diseases include, but not limited to, chronic obstructive pulmonary disease (COPD), including late-stage COPD, asthma, rheumatoid arthritis (RA), inflammatory bowel disease, chronic bronchitis, emphysema, septic shock, ulcerative colitis, Crohn's disease, adult or acute respiratory distress syndrome (ARDS), psoriasis, and the like. In another embodiment, compounds, compositions, and methods are described for treating and/or prevention of inflammatory diseases of the respiratory system.

It has been discovered herein that compounds described herein are capable of restoring HDAC2 activity. Without being bound by theory, it is believed herein that compounds described herein may increase HDAC promoter activity, may restore expression levels of HDAC2 and/or may decrease degradation of HDAC protein, such as degradation by proteosomes. It has also been discovered that compounds described herein decrease the production of inflammatory and proinflammatory agents, such as but not limited to IL-2, IL8, TNF-alpha, MMP-9, and the like, including HDAC mediated production of such inflammatory and proinflammatory agents.

It has also been discovered herein that compounds described herein are capable of reversing corticosteroid insensitivity, such as corticosteroid insensitivity that is observed in patients having inflammatory diseases that are being treated with corticosteroids, including patients being treated inflammatory diseases of the respiratory system such as COPD. In another embodiment, compounds, compositions, and methods are described for treating and/or prevention of inflammatory diseases in patients exhibiting corticosteroid insensitivity. In one variation, cotherapies for treating and/or prevention of inflammatory diseases in patients being treated with a corticosteroid are described that include the compounds, compositions, and methods described herein. In another embodiment, the disease is asthma. In another embodiment, the disease is rheumatoid arthritis. In another embodiment, the disease is COPD, including late stage COPD.

DETAILED DESCRIPTION

In another embodiment, compounds of the formula

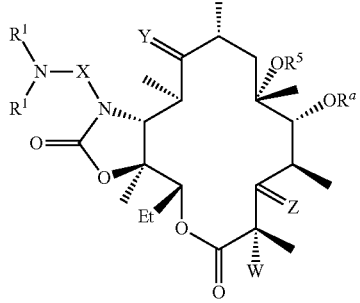

Formula (I)

or

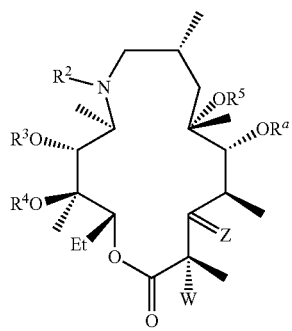

Formula (II)

and pharmaceutically acceptable salts, hydrates, or prodrugs thereof are described herein, wherein:

$R^1$ is in each instance independently selected from the group consisting of hydrogen, acyl, and alkyl, cycloalkyl, heteroalkyl, heterocyclyl, heterocyclylalkyl, heterocyclylheteroalkyl aryl, aryl alkyl, and arylheteroalkyl, each of which is optionally substituted; or $R^1$ are taken together with the attached nitrogen to form an optionally substituted heterocycle or optionally substituted heteroaryl; or $R^1$ are taken together with the attached nitrogen to form azido;

$R^2$ is acyl;

$R^3$ and $R^4$ are in each instance independently selected from the group consisting of hydrogen, acyl, and alkyl, cycloalkyl, heteroalkyl, heterocyclyl, heterocyclylalkyl, heterocyclylheteroalkyl aryl, aryl alkyl, and arylheteroalkyl, each of which is optionally substituted; or $R^3$ and $R^4$ are taken together with the attached oxygen atoms to form a carbonate;

$R^5$ is hydrogen, alkyl, alkenyl, or alkynyl;

$R^a$ is hydrogen, optionally substituted alkyl, acyl, or a saccharide; and

W is H or F;

X is alkylene, heteroalkylene, a divalent carbocycle, or a divalent heterocycle, each of which is optionally substituted;

Y taken together with the attached carbon forms a carbonyl, imine, oxime, or hydrazone, or Y represents H, $OR^5$; and Z taken together with the attached carbon forms a carbonyl, imine, oxime, or hydrazone, or Z represents $Z^a$, $OR^b$, where $Z^a$ is H; and $R^b$ is hydrogen, acyl, or a saccharide, or alkyl or arylalkyl, each of which is optionally substituted.

In another embodiment, compounds of the formula

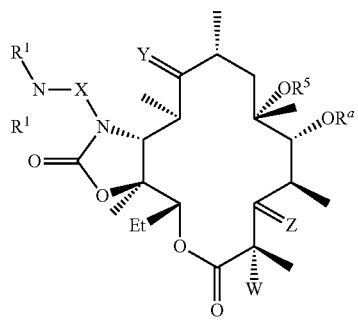

and pharmaceutically acceptable salts, hydrates, or prodrugs thereof are described herein, wherein:

$R^1$ is in each instance independently selected from the group consisting of hydrogen, acyl, and alkyl, cycloalkyl, heteroalkyl, heterocyclyl, heterocyclylalkyl, heterocyclylheteroalkyl aryl, aryl alkyl, and arylheteroalkyl, each of which is optionally substituted; or $R^1$ are taken together with the attached nitrogen to form an optionally substituted heterocycle or optionally substituted heteroaryl; or $R^1$ are taken together with the attached nitrogen to form azido;

$R^5$ is hydrogen, alkyl, alkenyl, or alkynyl;

$R^a$ is hydrogen, optionally substituted alkyl, acyl, or a saccharide; and

W is H or F;

X is alkylene, heteroalkylene, a divalent carbocycle, or a divalent heterocycle, each of which is optionally substituted;

Y taken together with the attached carbon forms a carbonyl, imine, oxime, or hydrazone, or Y represents H, $OR^5$; and Z taken together with the attached carbon forms a carbonyl, imine, oxime, or hydrazone, or Z represents $Z^a$, $OR^b$; where $Z^a$ is H; and $R^b$ is hydrogen, acyl, or a saccharide, or alkyl or arylalkyl, each of which is optionally substituted.

In another embodiment, compounds of the formula

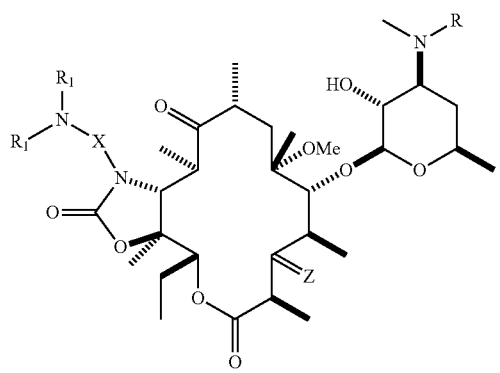

and pharmaceutically acceptable salts, hydrates, or prodrugs thereof are described herein, wherein X is alkylene; each $R^1$ is independently selected from H, optionally substituted alkyl, and acyl; and R is H or acyl, or alkyl, heteroalkyl, cycloalkyl, cycloheteroalkyl, arylalkyl, or heteroarylalkyl each of which is optionally substituted.

In another embodiment, compounds of the formula

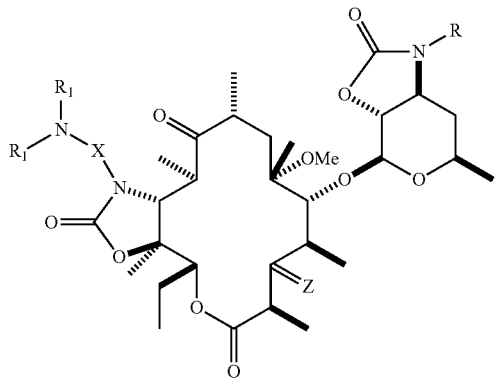

and pharmaceutically acceptable salts, hydrates, or prodrugs thereof are described herein, wherein X is alkylene; each $R^1$ is independently selected from H, optionally substituted alkyl, and acyl; and R is H or acyl, or alkyl, heteroalkyl, cycloalkyl, or cycloheterocyclyl, arylalkyl, or heteroarylalkyl each of which is optionally substituted.

In one variation of any of the foregoing embodiments of formula (I) and subgenera thereof, at least one $R^1$ is hydrogen. In another variation of any of the foregoing embodiments or variations, both $R^1$ are hydrogen. In another variation of any of the foregoing embodiments or variations, $R^1$ are taken together with the attached nitrogen to form an optionally substituted heteroaryl. In another variation of any of the foregoing embodiments or variations, $R^5$ is methyl. In another variation of any of the foregoing embodiments or variations, $R^a$ is a saccharide, such as a desosamine, or a derivative thereof. In another variation of any of the foregoing embodiments or variations, $R^a$ is a desosamine derivative having at least one nitrogen substituent other than methyl. In another variation of any of the foregoing embodiments or variations, $R^a$ is a desosamine derivative that includes NH. In another variation of any of the foregoing embodiments or variations, $R^a$ is a desosamine derivative that includes $NH_2$. In another variation of any of the foregoing embodiments or variations, $R^a$ is a desosamine derivative that includes an N-acyl. In another variation of any of the foregoing embodiments or variations, $R^a$ is a desosamine derivative that includes an N—($C_2$-$C_6$ alkyl or N—($C_3$-$C_6$ cycloalkyl), each of which is optionally substituted. In another variation of any of the foregoing embodiments or variations, $R^a$ is a nitrogen containing saccharide, such as a desosamine derivative, where the nitrogen has a conjugate acid pKa of less than about 8. In another variation of any of the foregoing embodiments or variations, W is H. In another variation of any of the foregoing embodiments or variations, W is F. In another variation of any of the foregoing embodiments or variations, X is alkylene, such as propylene, butylene, or pentylene. In another variation of any of the foregoing embodiments or variations, Y taken together with the attached carbon forms a carbonyl. In another variation of any of the foregoing embodiments or variations, Y taken together with the attached carbon forms a oxime of the formula $NOR^{11}$, wherein $R^{11}$ is hydrogen or optionally substituted alkyl. In another variation of any of the foregoing embodiments or variations, Z taken together with the attached carbon forms a carbonyl. In another variation of any of the foregoing embodiments or variations, Z represents $Z^a$, $OR^b$; where $Z^a$ is H, and $R^b$ is a saccharide, such as cladinose, or a derivative thereof. In another variation of any of the foregoing embodiments or variations, Z represents $Z^a$, $OR^b$; where $Z^a$ is H, and $R^b$ is an amino containing saccharide, or a derivative thereof.

It is to be understood that each of the foregoing variations of formula (I) may be combined in all chemically relevant ways. For example, the foregoing variations include a description of the subgenus of compounds where $R^1$ is H, $R^5$ is methyl, W is F, and Y and Z each form a carbonyl with the attached carbon. It is to be further understood that in the foregoing subgenus, $R^a$ may be hydrogen, optionally substituted alkyl, acyl, or a saccharide; or $R^a$ may be a saccharide, such as a desosamine, or a derivative thereof; or $R^a$ may be a desosamine derivative having at least one nitrogen substituent other than methyl; or $R^a$ may be a desosamine derivative that includes NH; or $R^a$ may be a desosamine derivative that includes an N-acyl; or $R^a$ may be a desosamine derivative that includes an N—($C_2$-$C_6$ alkyl or N—($C_3$-$C_6$ cycloalkyl), each of which is optionally substituted; or $R^a$ may be a nitrogen containing saccharide, such as a desosamine derivative, where the nitrogen has a conjugate acid pKa of less than about 8. It is to be further understood that other combinations are also described by the forgoing variations of formula (I).

In another embodiment, compounds of the formula

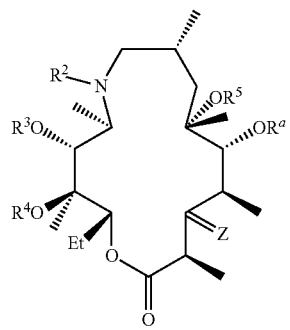

and pharmaceutically acceptable salts, hydrates, or prodrugs thereof are described herein, wherein:

$R^2$ is acyl;

$R^3$ and $R^4$ are in each instance independently selected from the group consisting of hydrogen, acyl, and alkyl, cycloalkyl, heteroalkyl, heterocyclyl, heterocyclylalkyl, heterocyclylheteroalkyl aryl, aryl alkyl, and arylheteroalkyl, each of which is optionally substituted; or $R^3$ and $R^4$ are taken together with the attached oxygen atoms to form a carbonate;

$R^5$ is hydrogen, alkyl, alkenyl, or alkynyl;

$R^a$ is hydrogen, optionally substituted alkyl, acyl, or a saccharide; and

Z taken together with the attached carbon forms a carbonyl, imine, oxime, or hydrazone, or Z represents $Z^a$, $OR^b$; where $Z^a$ is H; and $R^b$ is hydrogen, acyl, or a saccharide, or alkyl or arylalkyl, each of which is optionally substituted.

In another embodiment, compounds of the formula

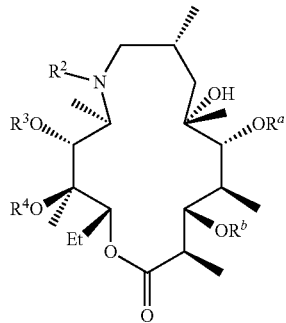

and pharmaceutically acceptable salts, hydrates, or prodrugs thereof are described herein.

In one variation of any of the foregoing embodiments of formula (II) and subgenera thereof, $R^2$ is hydrogen. In another variation of any of the foregoing embodiments or variations, $R^2$ is acyl. In another variation of any of the foregoing embodiments or variations, $R^2$ is an amino containing acyl, or a derivative thereof. In another variation of any of the foregoing embodiments or variations, $R^2$ is optionally substituted alkyl. In another variation of any of the foregoing embodiments or variations, $R^3$ and $R^4$ are both hydrogen. In another variation of any of the foregoing embodiments or variations, $R^3$ and $R^4$ are taken together with the attached oxygen atoms to form a carbonate.

In another variation of any of the foregoing embodiments or variations, $R^a$ is a saccharide, such as a desosamine, or a derivative thereof. In another variation of any of the foregoing embodiments or variations, $R^a$ is a desosamine derivative having at least one nitrogen substituent other than methyl. In another variation of any of the foregoing embodiments or variations, $R^a$ is a desosamine derivative that includes NH. In another variation of any of the foregoing embodiments or variations, $R^a$ is a desosamine derivative that includes $NH_2$. In another variation of any of the foregoing embodiments or variations, $R^a$ is a desosamine derivative that includes an N-acyl. In another variation of any of the foregoing embodiments or variations, $R^a$ is a desosamine derivative that includes an N—($C_2$-$C_6$ alkyl or N—($C_3$-$C_6$ cycloalkyl), each of which is optionally substituted. In another variation of any of the foregoing embodiments or variations, $R^a$ is a nitrogen containing saccharide, such as a desosamine derivative, where the nitrogen has a conjugate acid pKa of less than about 8. In another variation of any of the foregoing embodiments or variations, $R^b$ is hydrogen or acyl. In another variation of any of the foregoing embodiments or variations, $R^b$ is an amino containing acyl, or a derivative thereof. In another variation of any of the foregoing embodiments or variations, $R^b$ is a saccharide, such as cladinose, or a derivative thereof. In another variation of any of the foregoing embodiments or variations, $R^b$ is an amino containing saccharide, or a derivative thereof.

It is to be understood that each of the foregoing variations of formula (II) may be combined in all chemically relevant ways. For example, the foregoing variations include a description of the subgenus of compounds where $R^1$ is acyl; $R^3$ and $R^4$ are both hydrogen or $R^3$ and $R^4$ are taken together with the attached oxygen atoms to form a carbonate; and $R^b$ is a saccharide, such as cladinose, or a derivative thereof. It is to be further understood that in the foregoing subgenus, $R^a$ may be hydrogen, optionally substituted alkyl, acyl, or a saccharide; or $R^a$ may be a saccharide, such as a desosamine, or a derivative thereof; or $R^a$ may be a desosamine derivative having at least one nitrogen substituent other than methyl; or $R^a$ may be a desosamine derivative that includes NH; or $R^a$ may be a desosamine derivative that includes an N-acyl; or $R^a$ may be a desosamine derivative that includes an N—($C_2$-$C_6$ alkyl or N—($C_3$-$C_6$ cycloalkyl), each of which is optionally substituted; or $R^a$ may be a nitrogen containing saccharide, such as a desosamine derivative, where the nitrogen has a conjugate acid pKa of less than about 8. It is to be further understood that other combinations are also described by the forgoing variations of formula (II).

In another embodiment, compounds are described herein that have limited, substantially lack, or completely lack antibacterial activity. Illustratively, compounds of Formulae (I) and (II) where $R^a$ is a saccharide, such as desosamine, which includes a primary or secondary amino group instead of a tertiary amino group are appreciated to generally have limited, substantially lack, or completely lack antibacterial activity. Illustratively, compounds of Formulae (I) and (II) where $R^a$ is a not desosamine, not an amino containing saccharide, or not a saccharide are appreciated to generally have limited, substantially lack, or completely lack antibacterial activity. Without being bound by theory, it is believed herein that the higher polarity, lower lipophilicity, lower basicity, lower ability to engage in hydrogen bonding, and/or the presence of an active hydrogen may on the substituent contribute to the attenuation of the antibacterial activity of the compounds.

Illustratively, compounds of Formulae (I) and (II) where $R^a$ includes a sterically bulky group or substituent are appreciated to generally have limited, substantially lack, or completely lack antibacterial activity.

Illustratively, compounds of Formulae (I) and (II) where $R^a$ includes a desosamine or other amino containing saccharide, where the amino group is acylated are appreciated to generally have limited, substantially lack, or completely lack antibacterial activity.

Without being bound by theory, it is believed herein that the higher polarity, lower lipophilicity, lower basicity, lower ability to engage in hydrogen bonding, and/or the presence of an active hydrogen may on the substituent contribute to the attenuation of the antibacterial activity of the compounds. In one illustrative aspect, the pKa of the conjugate acid of the nitrogen is less than about 11, less than about 10, less than about 9, less than about 8.5, or less than about 8.

In each of the embodiments described herein, it is to be understood that the formulae include and represent not only all pharmaceutically acceptable salts of the compounds, but also include any and all hydrates and/or solvates of the compound formulae. It is appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non crystalline and/or amorphous forms of the compounds.

Illustrative derivatives described herein include, but are not limited to, both those compounds that may be synthetically prepared from the compounds described herein, as well as those compounds that may be prepared in a similar way as those described herein, but differing in the selection of starting materials. In a nonlimiting example, derivatives of amino groups include amide, carbamate, urea, and guanidine derivatives. In a nonlimiting example, derivatives of hydroxy groups include ether, ester, and carbamate derivatives.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may be include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that alkyl is advantageously of limited length, including $C_1$-$C_{24}$, $C_1$-$C_{12}$, $C_1$-$C_8$, $C_1$-$C_6$, and $C_1$-$C_4$. It is to be further understood that alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopenyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic groups, including aromatic carbocyclic and aromatic heterocyclic groups, each of which may be optionally substituted. As used herein, the term "carbaryl" includes aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, acylamino, and the like, each of which is optionally substituted. The term "amino derivative" also includes urea, carbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, acylcarbonyl, and the like, each of which is optionally substituted.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, and/or sulfonic acid is optionally substituted.

As used herein, the term "optionally substituted aryl" includes the replacement of hydrogen atoms with other functional groups on the aryl that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, and/or sulfonic acid is optionally substituted.

Illustrative substituents include, but are not limited to, a radical —$(CH_2)_xZ^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$—$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, and nitro; or $Z^X$ is selected from —$CO_2R^4$ and —$CONR^5R^6$, where $R^4$, $R^5$, and $R^6$ are each independently selected in each occurrence from hydrogen, $C_1$-$C_6$ alkyl, and aryl-$C_1$-$C_6$ alkyl.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —$CO_2H$, —$NR_2$. Illustrative prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, ($C_3$-$C_{20}$)alkanoyl; halo-($C_3$-$C_{20}$)alkanoyl; ($C_3$-$C_{20}$)alkenoyl; ($C_4$-$C_7$)cycloalkanoyl; ($C_3$-$C_6$)-cycloalkyl($C_2$-$C_{16}$)alkanoyl; optionally substituted aroyl, such as unsubstituted aroyl or aroyl substituted by 1 to 3 substituents selected from the group consisting of halogen, cyano, trifluoromethanesulphonyloxy, ($C_1$-$C_3$)alkyl and ($C_1$-$C_3$)alkoxy, each of which is optionally further substituted with one or more of 1 to 3 halogen atoms; optionally substituted aryl($C_2$-$C_{16}$)alkanoyl, such as the aryl radical being unsubstituted or substituted by 1 to 3 substituents selected from the group consisting of halogen, ($C_1$-$C_3$)alkyl and ($C_1$-$C_3$)alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, ($C_1$-$C_3$)alkyl, and ($C_1$-$C_3$)alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

The compounds described herein may be prepared as described herein using conventional processes. In addition, the described herein may be prepared as described in US Patent Application Publication No. 2006/0100164, in PCT International Publication No. WO 2009/055557, and in PCT International Publication No. WO 2010/048600, the disclosures of each of which are incorporated herein by reference in their entirety.

Illustratively, compounds that have limited, substantially lack, or completely lack antibacterial activity generally exhibit MIC50 values of >2, >4, >8, and/or >16 µg/mL in conventional assays against pathogenic organisms. However, it is to be understood that compounds that have limited, substantially lack, or completely lack antibacterial activity also generally do not exhibit clinically effective efficacy.

In another embodiment, compounds are described herein for treating inflammatory diseases, where the compounds are capable of activating HDAC2 promoter. In another embodiment, compounds are described herein for treating inflammatory diseases, where the compounds are capable of upregulating HDAC2 expression. In another embodiment, compounds are described herein for treating inflammatory diseases, where the compounds are capable of increasing the amount of HDAC2 protein present. In another embodiment, compounds are described herein for treating inflammatory diseases, where the compounds are capable of decreasing the degradation of HDAC2 protein, such as by proteases and/or proteosomes.

In another embodiment, compounds are described herein for treating inflammatory diseases, where the compounds are capable of inhibiting MMP9 production. In another embodiment, compounds are described herein for treating inflammatory diseases, where the compounds are capable of inhibiting IL-8 production. In another embodiment, compounds are described herein for treating inflammatory diseases, where the compounds are capable of inhibiting IL-2 production. In another embodiment, compounds are described herein for treating inflammatory diseases, where the compounds are capable of inhibiting TNF-alpha production. In another embodiment, compounds are described herein for treating inflammatory diseases, where the compounds are capable of inhibiting Atk phosphorylation.

In another embodiment, compositions are described herein that include (a) a therapeutically effective amount of one or more of the compounds described herein; and (b) one or more pharmaceutically acceptable carriers, diluents, and/or excipients. In one illustrative aspect, the therapeutically effective amount is an amount clinically effective for treating an inflammatory disease, such as an inflammatory disease of the respiratory system. In one embodiment, the disease is COPD.

In another embodiment, methods are describe herein that include the step of co-administering compounds described herein with other compounds, such as corticosteroids, other antibacterial agents, and the like.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a cotherapy.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, (21$^{st}$ ed., 2005)).

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and vehicles.

Illustratively, administering includes local use, such as when administered locally to the site of disease, injury, or defect. Illustrative local administration may be performed during open surgery, or other procedures when the site of disease, injury, or defect is accessible. Alternatively, local administration may be performed using parenteral delivery where the compound or compositions described herein are deposited locally to the site without general distribution to multiple other non-target sites in the patient being treated. It is further appreciated that local administration may be directly in the injury site, or locally in the surrounding tissue. Similar variations regarding local delivery to particular tissue types, such as organs, and the like, are also described herein. Illustratively, compounds may be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

Illustrative routes of oral administration include tablets, capsules, elixirs, syrups, and the like.

Illustrative routes for parenteral administration include intravenous, intraarterial, intraperitoneal, epidurial, intraurethral, intrasternal, intramuscular and subcutaneous, as well as any other art recognized route of parenteral administration. Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

EXAMPLES

The following compounds are illustrative, and non-limiting examples of the compounds generally described herein for treating inflammatory diseases.

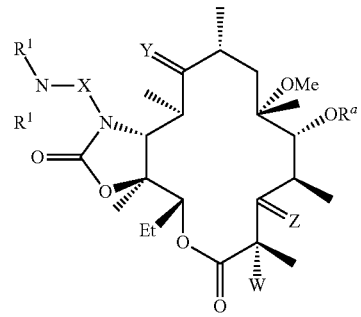

| Example | $(R^1)_2N$ | X | W | Y | Z | $R^a$ |
|---|---|---|---|---|---|---|
| 1 | $NH_2$ | $n\text{-}C_4H_8$ | H | O | O | desosamine |
| 2 | $NH_2$ | $n\text{-}C_4H_8$ | H | O | O | 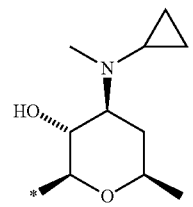 [SMILES: *[C@@H]1O[C@H](C)C[C@H](N(C)C2CC2)[C@H]1O] |

-continued

| Example | (R¹)₂N | X | W | Y | Z | Rᵃ |
|---|---|---|---|---|---|---|
| 3 | NH₂ | n-C₄H₈ | H | O | O | *(sugar with N-methyl-N-isopropylamino, HO, pyranose)* |
| 4 | NH₂ | n-C₄H₈ | H | O | O | *(sugar with N-methyl-N-cyclohexylamino, HO, pyranose)* |
| 5 | NH₂ | n-C₄H₈ | H | O | O | *(sugar with N-methyl-N-cyclobutylamino, HO, pyranose)* |
| 6 | NH₂ | n-C₄H₈ | H | O | O | *(sugar with N-methyl-N-(2-hydroxypropyl)amino, HO, pyranose)* |
| 7 | NEt₂ | n-C₅H₁₀ | H | O | O | desosamine |
| 8 | NHEt | n-C₄H₈ | H | O | O | desosamine |
| 9 | NMe₂ | n-C₄H₈ | H | O | O | desosamine |
| 10 | NMe₂ | n-C₂H₄ | H | O | O | desosamine |
| 11 | NEt₂ | n-C₂H₄ | H | O | O | desosamine |
| 12 | NEt₂ | n-C₄H₈ | H | O | H, OH | desosamine |
| 13 | NEt₂ | n-C₄H₈ | H | O | *(pyranose with H, *O, OH, OMe, Me)* | desosamine |
| 14 | NEt₂ | n-C₃H₆ | H | O | O | desosamine |
| 15 | NEt₂ | n-C₄H₈ | H | O | H, OH | *(oxazolidinone-fused pyranose)* |

-continued

| Example | (R¹)₂N | X | W | Y | Z | Rᵃ |
|---|---|---|---|---|---|---|
| 16 | NEt₂ | n-C₅H₁₀ | H | O | O | [structure: tetrahydropyran with N(Me)(iPr), OH, methyl] |
| 17 | N₃ | n-C₄H₈ | F | O | O | [structure: tetrahydropyran with NMe₂, OH, CH₂OAc] |
| 18 | N₃ | n-C₄H₈ | F | O | O | desosamine |
| 19 | N₃ | n-C₄H₈ | H | O | O | desosamine |
| 20 | N₃ | n-C₄H₈ | H | O | O | [structure: tetrahydropyran with NMe₂, two OH, methyl] |
| 21 | [2-pyridyl-triazole, N*] | n-C₄H₈ | H | O | O | [structure: tetrahydropyran with NMe₂, OH, methyl] |
| 22 | [benzotriazolylmethyl-triazole, N*] | n-C₄H₈ | F | O | O | desosamine |
| 23 | [2-pyridyl-triazole, N*] | n-C₄H₈ | H | O | O | [structure: tetrahydropyran with NHAc, OAc, OAc, methyl] |
| 24 | [Me₂NCH₂-triazole, N*] | n-C₄H₈ | H | O | H, [*O-tetrahydropyran with OMe, Me, OAc, Me] | desosamine |
| 25 | [HOCH₂-triazole, N*] | n-C₄H₈ | H | O | H, [*O-tetrahydropyran with OMe, Me, OAc, Me] | desosamine |

-continued

| Example | (R¹)₂N | X | W | Y | Z | Rᵃ |
|---|---|---|---|---|---|---|
| 26 | 2-pyridyl-triazolyl | n-C₄H₈ | H | O | O | tetrahydrofuran with OH, NH₂, CH₂-O-benzoyl |
| 27 | 2-pyridyl-triazolyl | n-C₄H₈ | F | O | O | tetrahydropyran with N(CH₃)₂, OH, methyl, O-C(=O)-NH-phenyl |

*indicates point of attachment

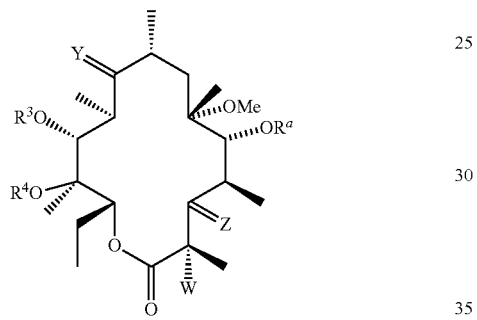

| Example | R³, R⁴ | W | Y | Rᵃ | Z |
|---|---|---|---|---|---|
| 28 | OH, OH | H | NOH | oxazolidinone-fused tetrahydropyran, N-methyl | H, OH |
| 29 | OH, OH | H | NOH | oxazolidinone-fused tetrahydropyran, N-benzyl | H, OH |
| 30 | OH, OH | H | O | oxazolidinone-fused tetrahydropyran, N-benzyl | H, OH |

-continued
| Example | R³, R⁴ | W | Y | Rᵃ | Z |
|---|---|---|---|---|---|
| 31 | OC(O)O | H | H, 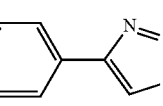 | desosamine | H, cladinose |
*indicates point of attachment
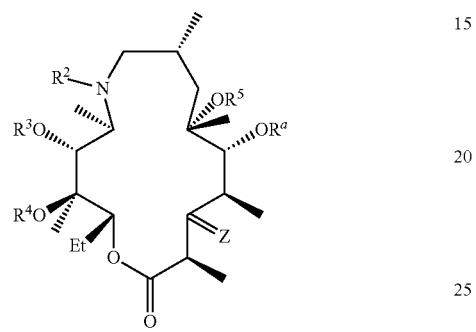
| Example | R² | R³, R⁴ | R⁵ | Rᵃ | Z |
|---|---|---|---|---|---|
| 32 | Ac | OC(O)O | H | desosamine | 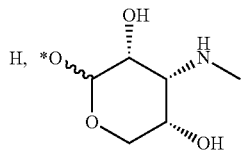 |
| 33 | Ac | OC(O)O | H | desosamine | H, cladinose |
| 34 | Ac | H, H | H | desosamine | 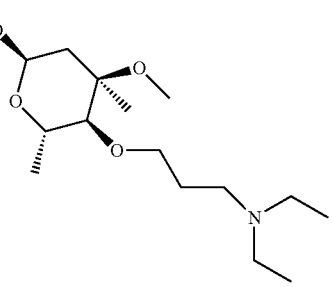 |
| 35 | Ac | OC(O)O | H | desosamine | 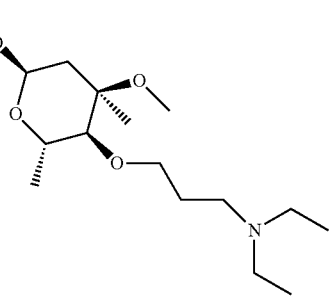 |

-continued
| Example | R² | R³, R⁴ | R⁵ | Rᵃ | Z |
|---|---|---|---|---|---|
| 36 | Ac | OC(O)O | H | desosamine | 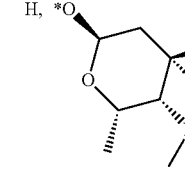 |
| 37 | Ac | OC(O)O | H | desosamine | 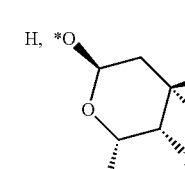 |
| 38 | Ac | H, H | H | desosamine | 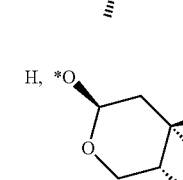 |
| 39 | Ac | OC(O)O | H | 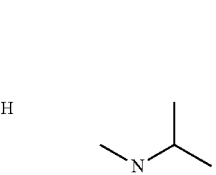 | 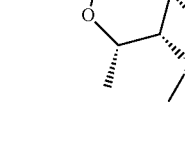 |
| 40 | Ac | OC(O)O | H | desosamine | 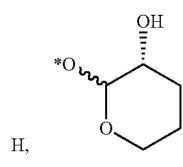 |
| 41 | 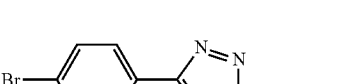 | H, H | Me | desosamine | O |
| 42 | Me | OC(O)O | H | desosamine | H, cladinose |
| 43 | Ac | H, H | H | 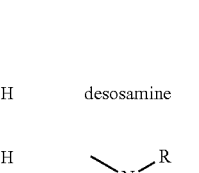 | 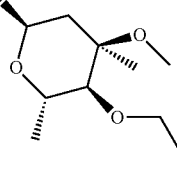 |

-continued

| Example | R² | R³, R⁴ | R⁵ | Rᵃ | Z |
|---|---|---|---|---|---|
| 44 | Ac | OC(O)O | H | (sugar with N(Me)R, HO, OH) | H, (sugar with OMe, O-propyl-NEt₂) |
| 45 | Ac | H, H | H | (sugar with N(Me)R, HO, OH) | H, (sugar with OMe, NR₂) |
| 46 | Ac | OC(O)O | H | (sugar with N(Me)R, HO, OH) | H, (sugar with OMe, NR₂) |
| 47 | Ac | H, H | H | (sugar with N(Me)R, HO, OH) | H, (sugar with OMe, CH₂NEt₂) |
| 48 | Ac | OC(O)O | H | (sugar with N(Me)R, HO, OH) | H, (sugar with OMe, CH₂NEt₂) |

*indicates point of attachment;

R is independently selected in each instance from hydrogen, alkyl, and acyl.

Reagents.

Telithromycin was provided by Cempra Pharmaceuticals, Inc. (Chapel Hill, N.C.). Erythromycin, clarithromycin, azithromycin, hydrogen peroxide, phorbol 12-myristate 13-acetate (PMA), lipopolysaccharide (LPS) were purchased from Sigma Aldrich. Recombinant Human TNF-α was purchased from R&D Systems Europe. The rabbit polyclonal anti-phospho-Akt1/2/3 (Ser 473)-R was obtained from Santa Cruz Biotechnology. The rabbit polyclonal anti-Akt1/PKBα was obtained from Millipore.

Cells.

The human monocytic cell line U937 and the human type II alveolar epithelial carcinoma cell line A549 were obtained from the American Type Culture Collection (ATCC, Rockville, Md.). PBMCs from COPD patients were obtained in Brompton hospital and separated by AccuSPIN (Sigma-Aldrich, Poole, UK). Cells were cultured in complete growth medium (Sigma-Aldrich) (RPMI 1640 for U937, PBMCs, and Dulbecco's modified essential medium (DMEM) for A549) supplemented with 10% fetal bovine serum (FBS) and 1% L-glutamine at 37° C. in a humidified atmosphere with 5% $CO_2$. U937 were differentiated into an adherent macrophage-like morphology by exposure to PMA (50 or 100 ng/ml) for 48 hrs in complete growth medium. Cell viability was assessed microscopically by trypan blue staining. Cell toxicity was determined by MTT assay as needed. This study was approved by the ethics committee of the Royal Brompton Hospitals, and all subjects gave written informed consent.

Method Example

Cytokine ELISA. LPS-induced IL-8, TNFα concentrations and TNFα-induced IL-8 concentrations are determined by sandwich ELISA according to the manufacturer's instructions (R&D Systems Europe). $IC_{50}$ values for dexamethasone on IL-8 production are calculated using the computer program Prism 4.0 (GraphPad Software Inc., San Diego, Calif.) as a marker for steroid sensitivity.

Method Example

Cell Lysis and Western Blotting. Whole cell protein extracts are prepared using modified RIPA buffer (50 mM Tris HCL pH 7.4, 0.5% NP-40, 0.25% Na-deoxycholate, 150 mM NaCl with freshly added complete protease (Roche). Phosphatase inhibitor (Active Motif) is also added when required. Protein concentration is determined using the Bio-Rad Protein Assay (Bio-Rad). Proteins are separated by SDS-PAGE under denaturing conditions, and electrotransferred to a nitrocellulose membrane (Amersham Biosciences, Amersham, U.K.) (Western blotting). The membranes are blocked in TBS containing 0.05% Tween 20 and 5% non-fat dried milk, and then incubated with anti-pAkt or Akt antibody followed by an horse radish peroxidase-conjugated secondary antibody (Dako UK Ltd., Ely, UK). Bound antibodies are visualized by ECL Plus (GE Healthcare UK Ltd., Little Chalfont, UK). The band density is calculated by densitometry (UVP Bioimaging Systems, Cambridge, UK) using Labworks software (Ultra-Violet Products, Cambridge, UK).

Method Example

In cell HDAC assay. Cells are incubated with Fluor de Lys™ substrate for 1 hr before lyses. Total HDAC activity from whole cell extracts is measured using the HDAC Fluorimetric Assay/Drug Discovery Kit (BIOMOL® International, Inc., Plymouth Meeting, Pa.).

Method Example

Preparations of cigarette smoke extract. To prepare the cigarette smoke extract, two full-strength Marlboro cigarettes (filters removed; Phillip Morris USA, Richmond, Va.) are combusted through a modified 60-ml syringe apparatus, and the smoke passed through 20 ml of DMEM medium. Each cigarette generally yields five draws of the syringe (to the 60-ml mark), with each individual draw taking approximately 10 s to complete. Cigarette smoke extract is then passed through a 0.20-μm filter to sterilize and remove particulate matter and is used immediately unless otherwise stated.

Method Example

Quantitative RT-PCR. Total RNA extraction and reverse transcription are performed using an RNeasy kit (QIAGEN, Crawley, UK) and a High-Capacity cDNA Reverse Transcription Kits (Applied Biosystems, Foster City, Calif.). Gene transcript level of HDAC2 (HS00231032_M1, Applied Biosystems, California, USA) and the house-keeping gene, guanine nucleotide binding protein beta polypeptide-2-like 1 (GNB2L1) (HS00272002_M1, Applied Biosystems) are quantified by real-time PCR using a TaqMan® Gene Expression Master Mix (Applied Biosystems) on a Rotor-Gene 6000 (Corbett Research, Cambridge, UK). Transcripts are analysed by the delta (D) CT method and variations in cDNA concentrations between different samples were corrected using GNB2L1.

Method Example

Zymography. MMP9 enzyme activity is measured by gelatin zymography. 5 μl of supernatants were diluted with 5 μl Laemli sample buffer (Bio-Rad) and are loaded on a Novex® 10% Zymogram (Gelatin) gel (Invitrogen). After electrophoresis (90 min, 125 V, 35 mA, 5 W) gels are incubated with 1× Novex® zymogram renaturing buffer (Invitrogen) for 30 min at room temperature with gentle agitation. Gels are then rinsed in 1× Novex® zymogram developing buffer (Invitrogen) for 30 min at room temperature with gentle agitation prior to overnight incubation in the developing buffer at 37° C. After incubation the gels are stained using the colloidal blue staining kit (Invitrogen) with buffer containing 20% methanol and 70% distilled water to visualize the zymogen bands. Relevant band intensities are quantified by densitometric analysis using the UVP GelDoc-It system.

Method Example

HDAC expression: HDAC2 promoter: U937 are transfected with HDAC2-luciferase plasmid and 4 hrs later cells are incubated with oxidative stress ($H_2O_2$, 200 μM) for 20 hrs. Promoter activation is evaluated by measuring luciferase intensity. Compounds are treated 20 min before oxidative stress treatment. As internal transfection control, β-gal is measured after β-gal plasmid transfection.

Method Example

Statistical analysis. Comparisons of two groups of data are performed using Student's t test. Other data are analyzed by one-way ANOVA with post hoc test, as appropriate. The difference is considered significant at $p<0.05$. Results are expressed as the mean±SEM.

Method Example

HDAC mRNA: Effect of compounds on HDAC2 mRNA level under oxidative stress ($H_2O_2$, 200 μM) in U937, is tested for confirmation (>50% inhibition of change in promoter activity). Total RNA is extracted 16 hrs after oxidative stress treatment. HDAC2 mRNA transcript level is evaluated by realtime QPCR using Taqman-system (Applied Biosystems). Compounds are treated 20 min before oxidative stress treatment. In one variation, in compounds that are highly positive, protein level is confirmed.

Method Example

HDAC expression: In cell HDAC activity assay: U937 is differentiated to macrophage type cells by PMA for 3 days. HDAC fluorescent substrate (Biomol) is added before exposure of oxidative stress ($H_2O_2$, 200 μM) or Tobacco smoke conditioned medium for 4 hrs. HDAC activity is measured (Biomol kit). Compounds at different concentrations are treated 20 min before oxidative stress treatment.

Method Example

HDAC2 promoter: U937 are differentiated to macrophage type cells by PMA for 3 days and transfected with HDAC2-luciferase plasmid and 4 hrs later cells are incubated with oxidative stress ($H_2O_2$, 200 μM) for 20 hrs. Promoter activation is evaluated by measuring luciferase intensity. Compounds are treated 20 min before oxidative stress treatment. As internal transfection control, β-gal is measured after β-gal plasmid transfection.

Method Example

HDAC2 mRNA: U937 is differentiated to macrophage type cells by PMA for 3 days and HDAC2 mRNA level is measured under oxidative stress ($H_2O_2$, 200 μM) and hypoxia. Total RNA is extracted 16 hrs after oxidative stress treatment. HDAC2 mRNA transcript level is evaluated by realtime QPCR using Taqman-system (Applied Biosystems). Compounds are treated 20 min before oxidative stress treatment.

Method Example

HDAC2 protein: U937 are differentiated to macrophage type cells by PMA for 3 days and HDAC2 protein expression is determined under oxidative stress ($H_2O_2$, 200 μM) and hypoxia by conventional western blotting. Nuclear protein is extracted 16 hrs after oxidative stress treatment. Compounds are treated 20 min before oxidative stress treatment.

Method Example

Inhibitory effect of macrolide on proinflammatory compound and protease production. U937 cells are treated with TNF-α with oxidative stress ($H_2O_2$, 200 μM) and supernatant is collected 24 hrs after stimulation. IL-8 production (as a COPD marker) is evaluated by ELISA (R&D). Compounds, or alternatively highly positive compounds, are evaluated for efficacy in a cytokine array (Tebu-bio). It is appreciated herein that multiple targets of the compounds described herein may be operating as a basis for the efficacy of the compounds.

Method Example

Anti-oxidant property of macrolides. In oxidative stress HDAC defect model, whether anti-oxidants are positive is confirmed. To confirm whether the compounds described herein have anti-oxidant properties, DCDHF oxidation by $H_2O_2$ and peroxynitrite is measured by index of oxidative stress. DCDHF substrate is incubated with test compound for 20 min and then stimulated with oxidative/nitrative stress, such as $H_2O_2$ (200 uM) or peroxynitrite (500 nM) is introduced into the tube. After 5 min, the oxidation level of DCDHF is measured by fluorescent microplate reader at 420 nm.

Method Example

Anti-inflammatory activity of compounds in vitro study: Differentiated-U937 cells are treated with TNF-α with oxidative stress ($H_2O_2$, 200 μM) and supernatant is collected 24 hrs after stimulation. IL-8 production (as a COPD marker) is evaluated by ELISA (R&D). For compounds, the efficacy in a cytokine array (Tebu-bio) is evaluated. It is appreciated herein that multiple targets of the compounds described herein may be operating as a basis for the efficacy of the compounds.

Method Example

Anti-inflammatory activity of macrolides in vivo study: A/J mice are exposed to LPS (200 ug/ml) intranasally. Test compounds are administered intranasally 1 hr before LPS challenge, and bronchoalveolar lavage is performed to detect inflammatory cells infiltration to lung. IL-8 (KC) levels are measured in bronchoalveolar lavage fluid. It has been observed that erythromycin and azithromycin have anti-inflammatory action in this in vivo model.

Method Example

Restoration of steroid sensitivity. U937 cells: U937 are treated with oxidative stress ($H_2O_2$, 200 μM or 0.15 dilution CSM (cigarette smoke conditioned medium)) and 4 hours later, stimulated with TNFα (10 ng/ml) in the presence of dexamethasone ($10^{-11}$-$10^{-6}$M). Supernatant and cells are collected 24 hrs after stimulation and IL-8 is measured by conventional ELISA. As the index of corticosteroid sensitivity, $IC_{50}$ of dexamethasone is calculated. Test compounds are treated 20 min before oxidative stress treatment.

Method Example

Peripheral blood mononuclear cells (PBMCs) from COPD: PBMCs are separated by AccuSpin column and are stimulated with TNFα (10 ng/ml) in the presence of dexamethasone ($10^{-11}$-$10^{-6}$M). Supernatant and cells are collected 24 hrs after stimulation and IL-8 is measured by conventional ELISA. As the index of corticosteroid sensitivity, $IC_{50}$ of dexamethasone is calculated. Test compounds are treated 20 min before oxidative stress treatment.

Method Example

Effects on steroid refractory airway inflammation in cigarette smoke-exposed mice The anti-inflammatory effect of compounds described herein are evaluated on mice exposed to smoking and compared with the effects of erythromycin and other commercially available macrolide antibiotics. C57BL6J (male, 6 weeks) are purchased from commercial suppliers, such as Japan Clear (Kanagawa, Japan) and adapted for 1 week. Mice (8) are exposed to cigarette smoke (4% cigarette smoke diluted with compressed air) for 30 min/day for 12 days using commercially marketed non-filtered cigarettes, such as Peace cigarettes (28 mg of tar and 2.3 mg of nicotine per cigarette; Japan Tobacco Inc.) by a Tobacco Smoke Inhalation Experiment System for small animals (for example, INH06-CIGR02A, MIPS, Osaka, Japan). Compounds described herein are suspended into 0.5% methylcellulose (4000 CP) with 0.2% tween80, and orally and therapeutically administered for 3 days after the last day of cigarette smoke exposure (for example, 50 mg/kg, po daily). Comparison compounds, such as erythromycin and prednisolone are similarly administered. On the day after final drug treatment, mice are sacrificed for bronchoalveolar lavage (BAL), and lung tissue is collected for assay. BAL is measured for total cell, macrophage, and neutrophil count. BALF is assayed by MMP9 zymography, and in a KC and IL-8 assay. Lung tissue is assayed for HDAC expression, HDAC promoter level, and HDAC protein level. PCR is used to evaluate MMP9, KC, and TNFα. Additional details are described in Nakamaru et al, FASEB J (2009).

Method Example

Effects of compounds on $H_2O_2$-induced reduction of HDAC activity in PMA-differentiated U937 cells. PMA-differentiated macrophage-like cells are pretreated with compounds described herein for 20 min. After $H_2O_2$ (200 µM) stimulation for 4 hrs, HDAC activity is assayed. Data are expressed as fold changes against positive control treated with $H_2O_2$ only. Values represent means of four experiments±SEM. Example 33 restores the $H_2O_2$-induced reduction (positive control) in HDAC activity in PMA differentiated U937 cells (macrophage type) at concentrations of about 10 µM or greater, and with statistical significance of $p<0.01$ versus treatment with $H_2O_2$ only (one-way ANOVA with post hoc test, n=4) at doses of about 30 µM or greater. In addition, the HDAC activity of cells treated with Example 33 is higher than untreated controls (negative control), with statistical significance. Restoration of HDAC activity is observed with ERY (erythromycin), CLR (clarithromycin), AZI (azithromycin) and TEL (telithromycin) only at much higher doses than Example 33, and at the highest doses tested, ERY, CLR, AZI, and TEL only restore HDAC activity to levels comparable to untreated controls. Example 1 also restores the $H_2O_2$-induced reduction in HDAC activity at concentrations of about 100 µM or greater.

Method Example

Effects of macrolides on cigarette smoke extract-induced (CSE-induced) reduction of HDAC2 mRNA in A549 cells. Cells pretreated with compounds described herein for 30 min are exposed to CSE (0.15 O.D.) for 1 hr. The cells are washed twice and incubated with medium only for 4 hrs. Data are expressed as % reduction from baseline (left) or % increase from baseline under $H_2O_2$. Values represent means of three experiments±SEM. Example 33 reverses cigarette smoke extract-induced (CSE-induced) reduction of HDAC2 mRNA expression in A549 cells at concentrations of about 10 µM or greater, and with statistical significance of $p<0.05$ versus treatment with CSE only (one-way ANOVA with post hoc test, n=3) at doses of about 30 µM or greater. Reversal of HDAC mRNA expression reduction is observed with ERY (erythromycin) only at much higher doses than Example 33.

Method Example

Effects of compounds on $H_2O_2$-induced phosphorylation of Akt in PMA-differentiated U937 cells. PMA-differentiated macrophage-like cells are pretreated with compounds described herein for 20 min. After $H_2O_2$ (1 mM) stimulation for 30 min, cells are lysed. Phosphorylation levels of Akt are measured by western blot. Data are calculated relative to total protein, and expressed as fold changes against positive control treated with $H_2O_2$ only. Values represent means of three or four experiments±SEM. Akt is significantly phosphorylated by $H_2O_2$ (1 mM) stimulation for 30 min. Without being bound by theory, it is believed herein that the phosphorylation of Akt suggests PI3K activation. Example 33 concentration-dependently inhibits Akt phosphorylation at concentrations of about 30 µM or greater, and with statistical significance of $p<0.05$ versus treatment with $H_2O_2$ only (one-way ANOVA with post hoc test, n=3 or 4) at doses of about 100 µM or greater. Inhibition of Akt phosphorylation is observed with ERY at comparable concentrations, but with CLR, AZI, and TEL only at much higher concentrations than Example 33. Example 1 also inhibits Akt phosphorylation at concentrations of about 30 µM or greater.

Method Example

Effects of compounds on LPS-induced IL-8 and TNFα release in PMA-differentiated U937 cells. PMA-differentiated macrophage-like cells are pretreated with compounds described herein for 1 hr, followed by LPS (100 ng/ml) stimulation for 4 hrs. LPS-induced IL-8 and TNFα release is evaluated by ELISA. Values represent means of three experiments±SEM. LPS significantly increases IL-8 production in PMA-differentiated U937 cells. Example 33 inhibits LPS-induced IL-8 release at concentrations of about 100 µM or greater, with statistical significance of $p<0.05$ versus treatment with $H_2O_2$ only (one-way ANOVA with post hoc test, n=3). Inhibition of LPS-induced IL-8 release is observed only with CLR at higher concentrations than Example 33, and ERY, AZI, and TEL did not show any inhibition at any concentration tested. Example 33 inhibits both LPS-induced TNFα release at concentrations of about 100 µM or greater, with statistical significance of $p<0.01$ versus treatment with $H_2O_2$ only (one-way ANOVA with post hoc test, n=3). Inhibition of LPS-induced TNFα release is observed only with CLR and TEL at higher concentrations than Example 33, and ERY and AZI and did not show any inhibition at any concentration tested.

Method Example

Effects of compounds on PMA-induced MMP9 expression in U937 cells. U937 cells are pretreated with compounds described herein for 1 hr, followed by PMA (50 ng/ml) treatment for 48 hrs. After 48 hrs supernatants are collected for zymography. MMP9 enzyme activity is measured by gelatin zymography. Data are expressed as fold changes against positive control treated with PMA only. Values represent means of three experiments±SEM. Example 33 inhibits PMA-induced MMP9 up-regulation at concentrations of about 33 µM or greater, with statistical significance of p<0.05 versus treatment with PMA only (one-way ANOVA with post hoc test, n=3) at concentrations of about 100 µM or greater. Example 1 also inhibits PMA-induced MMP9 up-regulation at concentrations of about 300 µM or greater.

IC50 of compounds on LPS-induced IL-8 release, LPS-induced TNFα release, and PMA-induced MMP9 expression in PMA-differentiated U937 cells.

|  | Example 33 | CLR | TEL |
|---|---|---|---|
| IL-8 IC50 (µM) | 95 ± 14** | 507 ± 44 | NA |
| TNFα IC50 (µM) | 97 ± 5* | 426 ± 64 | 231 ± 37 |
| MMP9 IC50 (µM) | 56 ± 19 | NA | NA |

**p < 0.01 versus CLR, *p < 0.01 versus TEL, *p < 0.05 versus CLR (unpaired t test, n = 3); NA = inactive.

Method Example

Effects of compounds on $H_2O_2$-induced steroid insensitivity in U937 cells. Cells stimulated with $H_2O_2$ (200 µM) overnight are incubated with compounds described herein for 30 min under $H_2O_2$ (200 µM) exposure. The cells are treated with dexamethasone ($10^{-11}$ to $10^{-6}$ M) for 20 min, followed by the TNFα stimulation overnight. TNFα-induced IL-8 release is evaluated by ELISA and $IC_{50}$ values for dexamethasone on IL-8 production are calculated using Prism. Data are expressed as fold changes against positive control treated with $H_2O_2$ only. Values represent means of four experiments±SEM. $H_2O_2$ exposure reduces dexamethasone sensitivity by approximately 4 fold based on calculated IC50 values of TNFα-induced IL-8 production. None of ERY, CLR, or AZI restored dexamethasone sensitivity at the highest concentration tested (100 µM).

Method Example

Effects of compounds on steroid sensitivity in PBMCs from COPD patients. Cells are incubated with compounds described herein for 30 min. The cells are treated with dexamethasone ($10^{-11}$ to $10^{-6}$ M) for 20 min, followed by the TNFα stimulation overnight. TNFα-induced IL-8 release is evaluated by ELISA and $IC_{50}$ values for dexamethasone on IL-8 production are calculated using Prism. Data are expressed as fold changes against non-treatment control. Values represent means of four experiments±SEM. ERY and CLR decreased the $IC_{50}$ value for dexamethasone (restored steroid sensitivity) at to highest concentrations tested (100 µM).

| | Example | | | | | | |
|---|---|---|---|---|---|---|---|
| | 32 | 1 | 21 | 40 | 41 | 31 | 22 |
| MMP9 inhibition (%) | 40 (49) | 55 (43) | 49 (41) | 60 (38) | 39 (41) | 21 (40) | 38 (23) |
| HDAC reduction (% restoration) | 79 (65) | 68 (53) | 36 | 26 | 14 | −17 | 22 (29) |
| TNFα inhibition (%) | 73 | 73 | 14 | 68 | 45 | 24 | 48 |
| IL-8 inhibition (%) | 55 | 72 | 59 | 93 | 54 | 53 | 76 |
| Cell Toxicity (% cell death) | 11 | 6 | 3 | 26 | 8 | 0 | 11 |
| MICs | | | | | | | |
| K. pneumonia 13883 | >64 | >64 | >64 | >64 | >64 | >64 | >64 |
| E. coli ATCC 25922 | >64 | >64 | | >64 | >64 | >64 | >64 |
| S. typhimurium ATCC 14028 | >64 | >64 | | >64 | >64 | >64 | 64 |
| H. influenzae ATCC 49247 | | >64 | >64 | >64 | >64 | 32 | 2 |
| H. influenzae LC002 | | >64 | >64 | | | | |
| S. pneumoniae ATCC 49619 | 32 | ≤0.125 | >64 | 64 | 32 | ≤0.125 | ≤0.125 |
| S. pneumoniae 163 (MefA) | | 0.5, 1 | | | | | 64 |
| S. pneumoniae 303 (ErmB) | | >64 | | | | | ≤0.125 |
| S. pneumoniae 3773 (ErmB) | | | | | | | |
| S. aureus ATCC 29213 (MSSA) MLS-S | 32 | 8 | >64 | 16 | 64 | 4 | ≤0.125 |
| S. aureus MRSA 33591 | | >64 | >64 | | >64 | >64 | >64 |
| S. aureus 96:11480 (MLS-I) | | 8 | | | | | ≤0.125 |
| S. pyogenes ATCC 19615 | | 0.25, 0.5 | | >64 | 64 | 0.25 | ≤0.125 0.25 |
| S. pyogenes ATCC 1721 | | | | | | | |
| P. aeruginosa ATCC 27853 | >64 | | | >64 | >64 | >64 | >64 |
| N. gonorrhoeae ATCC 49226 | | | | 8, 16 | 64 | | 0.25 |
| E. faecalis ATCC 29212 | 32 | | | 32 | | 16, 32 | |
| E. faecium ATCC 19434 | | 4 | >64 | | 64 | | ≤0.125 |

| | Example | | | | | | | |
|---|---|---|---|---|---|---|---|---|
| | 23 | 42 | 24 | 25 | 26 | 27 | AZI | CLR |
| MMP9 inhibition (%) | 32 (31) | −2 | 11 | 10 | 2 | 1 | 33 (25) | 8 (22) |
| HDAC reduction (% restoration) | −13 | 104 (79) | 85 | 72 (63) | 92 | 75 | 34 | 14 |
| TNFα inhibition (%) | 76 | 8 | 6 | 15 | −25 | 34 | 31 | 21 |
| IL-8 inhibition (%) | 13 | −27 | 60 | 26 | −51 | −43 | 44 | 17 |
| Cell Toxicity (% cell death) | 9 | −8 | −3 | −8 | −2 | −7 | −16 | −7 |
| MICs | | | | | | | | |
| K. pneumonia 13883 | >64 | 8-32 | | | | | | |
| E. coli ATCC 25922 | | 8-32 | | | | | | |
| S. typhimurium ATCC 14028 | | 8-16 | | | | | | |
| H. influenzae ATCC 49247 | >64 | 4 | 64 | 4 | >64 | >64 | | |
| H. influenzae LC002 | >64 | | | | | | | |
| S. pneumoniae ATCC 49619 | 4 | ≤0.125 | | | 32 | 32 | | |

-continued

| | | | | |
|---|---|---|---|---|
| S. pneumoniae 163 (MefA) | 2 | | 64 | 8 |
| S. pneumoniae 303 (ErmB) | 16 | | | >64 |
| S. pneumoniae 3773 (ErmB) | | | >64 | >64 |
| S. aureus ATCC 29213 (MSSA) MLS-S | >64 | 1 | | |
| S. aureus MRSA 33591 | >64 | >64 | | |
| S. aureus 96:11480 (MLS-I) | >64 | | | |
| S. pyogenes ATCC 19615 | 16 | ≤0.125 | | |
| S. pyogenes ATCC 1721 | | | >64 | >64 |
| P. aeruginosa ATCC 27853 | | >64 | | |
| N. gonorrhoeae ATCC 49226 | | ≤0.125 | | |
| E. faecalis ATCC 29212 | | | | |
| E. faecium ATCC 19434 | 16 | 8 | | |

What is claimed is:

1. A pharmaceutical composition comprising (a) a therapeutically effective amount of one or more compounds of the formula

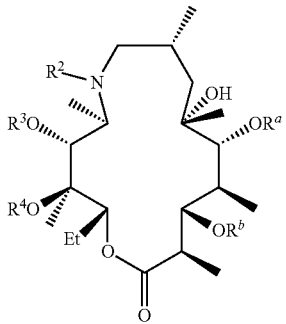

or a pharmaceutically acceptable salt thereof, wherein:
R² is acyl;
R³ and R⁴ are taken together with the attached oxygen atoms to form a carbonate;
R⁵ is hydrogen, alkyl, alkenyl, or alkynyl;
Rᵃ is hydrogen, optionally substituted alkyl, acyl, or a monosaccharide; and
Z taken together with the attached carbon forms a carbonyl, imine, oxime, or hydrazone, or Z represents Zᵃ, ORᵇ; where Zᵃ is H; and Rᵇ is hydrogen, acyl, or a monosaccharide, or alkyl or arylalkyl, each of which is optionally substituted; and
(b) a carrier, diluent, or excipient, or a combination thereof;
where the composition is adapted for treating an inflammatory disease of the respiratory system.

2. The composition of claim 1, wherein at least one compound is of the formula

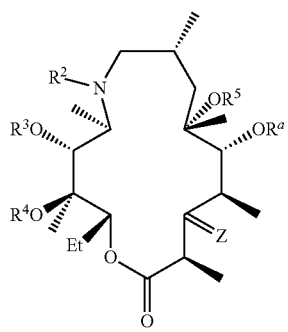

or a pharmaceutically acceptable salt thereof.

3. The composition of claim 1, wherein R² is acetyl; and R³ and R⁴ are taken together with the attached oxygen atoms to form a carbonate.

4. The composition of claim 1 wherein the disease is selected from the group consisting of chronic obstructive pulmonary disease (COPD), asthma, chronic bronchitis, emphysema, and acute respiratory distress syndrome (ARDS).

5. A pharmaceutical composition comprising (a) a therapeutically effective amount of one or more compounds of the formula

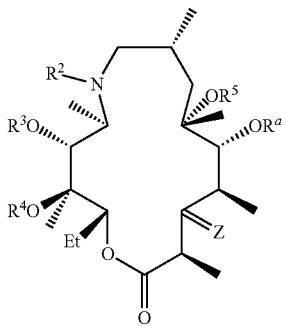

or a pharmaceutically acceptable salt thereof, wherein:
R² is acyl;
R³ and R⁴ are in each instance independently selected from the group consisting of hydrogen, acyl, and alkyl, cycloalkyl, heteroalkyl, heterocyclyl, heterocyclylalkyl, heterocyclylheteroalkyl aryl, aryl alkyl, and arylheteroalkyl, each of which is optionally substituted; or R³ and R⁴ are taken together with the attached oxygen atoms to form a carbonate;
R⁵ is hydrogen, alkyl, alkenyl, or alkynyl;

R$^a$ is hydrogen, optionally substituted alkyl, acyl, or a monosaccharide; and

Z taken together with the attached carbon forms a carbonyl, imine, oxime, or hydrazone, or Z represents Z$^a$, OR$^b$; where Z$^a$ is H; and R$^b$ is an amino containing acyl, or a derivative thereof; and (b) a carrier, diluent, or excipient, or a combination thereof;

where the composition is adapted for treating an inflammatory disease of the respiratory system.

6. The composition of claim 5, wherein R$^3$ and R$^4$ are both hydrogen.

7. The composition of claim 5 wherein the disease is selected from the group consisting of chronic obstructive pulmonary disease (COPD), asthma, chronic bronchitis, emphysema, and acute respiratory distress syndrome (ARDS).

8. A method for treating an inflammatory disease of the respiratory system in a patient, the method comprising administering to the patient a therapeutically effective amount of a pharmaceutical composition comprising (a) at least one compound is of the formula

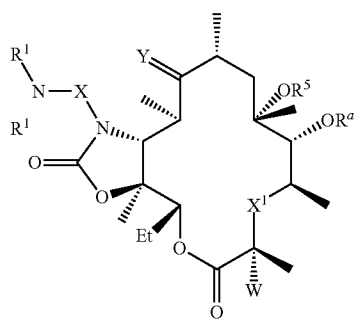

or a pharmaceutically acceptable salt thereof, wherein:
R$^1$ is in each instance independently selected from the group consisting of hydrogen, acyl, and alkyl, cycloalkyl, heteroalkyl, heterocyclyl, heterocyclylalkyl, heterocyclylheteroalkyl aryl, aryl alkyl, and arylheteroalkyl, each of which is optionally substituted; or R$^1$ are taken together with the attached nitrogen to form an optionally substituted heterocycle or optionally substituted heteroaryl; or R$^1$ are taken together with the attached nitrogen to form azido;

R$^5$ is hydrogen, alkyl, alkenyl, or alkynyl;

R$^a$ is hydrogen, optionally substituted alkyl, acyl, or a monosaccharide; and

W is H or F;

X is alkylene, heteroalkylene, a divalent carbocycle, or a divalent heterocycle, each of which is optionally substituted;

Y taken together with the attached carbon forms a carbonyl, imine, oxime, or hydrazone, or Y represents H, OR$^5$; and X$^1$ is C=Z, where Z taken together with the attached carbon forms a carbonyl, imine, oxime, or hydrazine; or X$^1$ is CHOR$^b$, where R$^b$ is hydrogen, or acyl, or a monosaccharide, or alkyl or arylalkyl, each of which is optionally substituted; and (b) optionally one or more carriers, diluents, or excipients, or a combination thereof.

9. The method of claim 8, wherein at least one of R$^1$ is hydrogen.

10. The method of claim 8, wherein at least one of R$^1$ is acyl group.

11. The method of claim 8, wherein at least one of R$^1$ is C$_2$-C$_6$ alkyl or C$_3$-C$_6$ cycloalkyl, each of which is optionally substituted.

12. The method of claim 8, wherein both R$^1$ are hydrogen and R$^a$ is a monosaccharide.

13. The method of claim 8, wherein R$^a$ is an optionally substituted desmethyl or bisdesmethyl desosamine.

14. The method of claim 13, at least one of R$^1$ is hydrogen.

15. The method of claim 13, wherein at least one of R$^1$ is acyl group.

16. The method of claim 15, wherein at least one R$^1$ is hydrogen.

17. The method of claim 13, wherein at least one of R$^1$ is C$_2$-C$_6$ alkyl or C$_3$-C$_6$ cycloalkyl, each of which is optionally substituted.

18. The method of claim 8, wherein X is alkylene.

19. The method of claim 8, wherein X$^1$ is CHOR$^b$, where R$^b$ is an amino containing monosaccharide.

20. The method of claim 8 wherein the disease is selected from the group consisting of chronic obstructive pulmonary disease (COPD), asthma, chronic bronchitis, emphysema, and acute respiratory distress syndrome (ARDS).

21. A method for treating an inflammatory disease of the respiratory system in a patient, the method comprising administering to the patient a therapeutically effective amount of a pharmaceutical composition comprising (a) one or more compounds of the formula

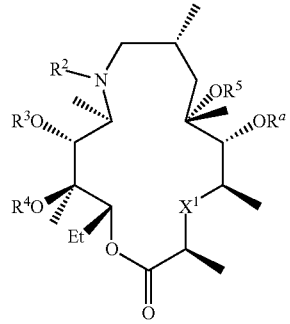

or a pharmaceutically acceptable salt thereof, wherein
R$^2$ is acetyl;

R$^3$ and R$^4$ are in each instance independently selected from the group consisting of hydrogen, acyl, and alkyl, cycloalkyl, heteroalkyl, heterocyclyl, heterocyclylalkyl, heterocyclylheteroalkyl aryl, aryl alkyl, and arylheteroalkyl, each of which is optionally substituted; or R$^3$ and R$^4$ are taken together with the attached oxygen atoms to form a carbonate;

R$^5$ is hydrogen, alkyl, alkenyl, or alkynyl;

R$^a$ is hydrogen, optionally substituted alkyl, acyl, or a monosaccharide; and

X$^1$ is C=Z, where Z taken together with the attached carbon forms a carbonyl, imine, oxime, or hydrazine; or X$^1$ is CHOR$^b$, where R$^b$ is hydrogen, or acyl, or a monosaccharide, or alkyl or arylalkyl, each of which is optionally substituted; and (b) optionally one or more carriers, diluents, or excipients, or a combination thereof.

22. The method of claim 21, wherein at least one compound is of the formula

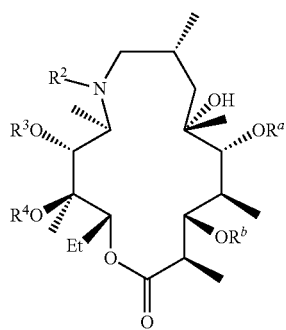

or a pharmaceutically acceptable salt thereof.

23. The method of claim 22, wherein $R^3$ and $R^4$ are both hydrogen.

24. The method of claim 21, wherein $R^3$ and $R^4$ are both hydrogen.

25. The method of claim 21, wherein $R^3$ and $R^4$ are taken together with the attached oxygen atoms to form a carbonate.

26. The method of claim 21, wherein $X^1$ is $CHOR^b$, where $R^b$ is an amine, amide, carbamate, urea, or guanidine containing acyl.

27. The method of claim 26, wherein $R^3$ and $R^4$ are taken together with the attached oxygen atoms to form a carbonate.

28. The method of claim 21 wherein the disease is selected from the group consisting of chronic obstructive pulmonary disease (COPD), asthma, chronic bronchitis, emphysema, and acute respiratory distress syndrome (ARDS).

29. A compound of the formula

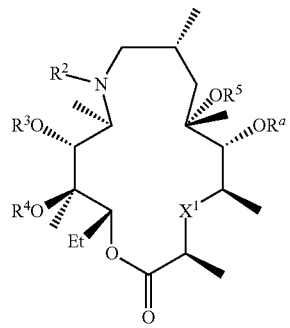

or a pharmaceutically acceptable salt thereof, wherein:
  $R^2$ is acyl;
  $R^3$ and $R^4$ are taken together with the attached oxygen atoms to form a carbonate;
  $R^5$ is hydrogen, alkyl, alkenyl, or alkynyl;
  $R^a$ is hydrogen, optionally substituted alkyl, acyl, or a monosaccharide; and
  $X^1$ is C=Z, where Z taken together with the attached carbon forms a carbonyl, imine, oxime, or hydrazine; or $X^1$ is $CHOR^b$, where $R^b$ is hydrogen, or acyl, or a monosaccharide, or alkyl or arylalkyl, each of which is optionally substituted.

* * * * *